United States Patent
Watanabe et al.

(10) Patent No.: US 8,034,403 B2
(45) Date of Patent: Oct. 11, 2011

(54) METHOD FOR FORMING COPPER DISTRIBUTING WIRES

(75) Inventors: Mikio Watanabe, Shizuoka-ken (JP); Hideaki Zama, Shizuoka-ken (JP)

(73) Assignee: Ulvac, Inc., Kanagawa (JP)

( * ) Notice: Subject to any disclaimer, the term of this patent is extended or adjusted under 35 U.S.C. 154(b) by 1040 days.

(21) Appl. No.: 11/663,807

(22) PCT Filed: Sep. 12, 2005

(86) PCT No.: PCT/JP2005/016712
§ 371 (c)(1),
(2), (4) Date: Sep. 4, 2007

(87) PCT Pub. No.: WO2006/035591
PCT Pub. Date: Apr. 6, 2006

(65) Prior Publication Data
US 2010/0291290 A1    Nov. 18, 2010

(30) Foreign Application Priority Data

Sep. 27, 2004   (JP) .................................. 2004-279365

(51) Int. Cl.
*B05D 5/12*   (2006.01)
(52) U.S. Cl. ... 427/117; 427/118; 427/250; 427/255.31; 427/255.36; 427/96.6
(58) Field of Classification Search .................. 427/117, 427/118, 250, 255.31, 255.36, 96.6
See application file for complete search history.

(56) References Cited

U.S. PATENT DOCUMENTS

| | | | |
|---|---|---|---|
| 6,424,036 B1* | 7/2002 | Okada ........................... | 257/734 |
| 7,291,558 B2* | 11/2007 | Geffken et al. ............... | 438/687 |
| 2003/0082301 A1* | 5/2003 | Chen et al. ............... | 427/255.28 |
| 2005/0080282 A1* | 4/2005 | Kadota et al. .................... | 556/10 |
| 2006/0105570 A1* | 5/2006 | Hautala et al. ................ | 438/687 |
| 2009/0263965 A1* | 10/2009 | Gordon et al. ................ | 438/643 |

FOREIGN PATENT DOCUMENTS

| | | |
|---|---|---|
| JP | 8-222568 A | 8/1996 |
| JP | 11-217673 A | 8/1999 |
| JP | 2003-017437 A | 1/2003 |
| JP | 2003-522827 A | 7/2003 |
| JP | 2003-252823 A | 9/2003 |
| JP | 2003-292495 A | 10/2003 |
| WO | 03/038892 A2 | 5/2003 |
| WO | WO 03/064437 * | 8/2003 |

OTHER PUBLICATIONS

Molares, Maria, et al., "Singl-Crystalline Copper Nanowires Produced by Electrochemical Deposition in Polymeric Ion Track Membranes". Advanced Materials, 2001, 13, No. 1, Jan. 5.*

* cited by examiner

*Primary Examiner* — Bret Chen
(74) *Attorney, Agent, or Firm* — Arent Fox, LLP

(57) ABSTRACT

A method of forming a primary coat, which consists of a V- or Ti-containing film, formed on the surface of a subject on which holes or the like have been formed, according to the CVD technique, while using, for instance, a tetravalent amide-type vanadium-containing organometal compound as a raw gas and using, for instance, tertiary butyl hydrazine as a reducing gas, and a copper-containing film is then formed on the primary coat, according to the CVD technique, to thus fill the holes or the like with the copper-containing film and to thus form copper distributing wire, which is excellent in the hole-filling properties and excellent in the adhesion to a primary coat, this process can be applied to the field of copper distributing wires used in the semiconductor industries.

25 Claims, 4 Drawing Sheets

To Reaction Chamber 301

To Reaction Chamber 301

To Reaction Chamber 301

METHOD FOR FORMING COPPER DISTRIBUTING WIRES

CROSS-REFERENCE TO RELATED APPLICATION

This application is a National Stage entry of International Application Number PCT/JP2005/016712, filed Sep. 12, 2005. The disclosure of the prior application is hereby incorporated herein in its entirety by reference.

TECHNICAL FIELD

The present invention relates to a method for forming copper distributing wires or copper interconnections and, in particular, to a method for forming copper distributing wires, which comprises the step of forming a copper-containing film, by the CVD technique, on a primary coat or under coat consisting of a vanadium- or titanium-containing film formed according to the CVD technique.

BACKGROUND ART

With respect to the distributing wires required when fabricating a semiconductor element (such as an LSI or IC element or the like), it is common that a barrier and/or adherent layer as a primary coat in or on contact holes and grooves which permit the connection between lower and upper distributing wires. This barrier layer has frequently been formed, between layers of a wire material and an insulating material, for the purpose of preventing any mutual diffusion between the wire material and the insulating material and hence preventing the occurrence of any deterioration of the characteristic properties of such a semiconductor element, while the adherent later has likewise frequently been formed, between layers of a wire material and an insulating material, for the purpose of preventing any peeling of films at the boundary between the layers of the wire material and the insulating material.

There has recently been proposed the use of a copper material having a lower specific resistance as a material for forming distributing wires within contact holes and/or grooves, in place of the conventionally used Al materials. In this case, a barrier layer is formed between copper distributing wires and a silicon oxide film or the like, in order to prevent any diffusion of copper into an insulating layer consisting of, for instance, a silicon oxide film serving as a primary coat for the copper distributing wires.

Incidentally, there has conventionally been used the plating technique in the formation of such copper distributing wires described above. However, the size of contact holes or the like has become longer and narrower as the reduction of the scale of the distributing wires of, for instance, LSI elements, and an additional problem arises, such that it would be difficult for a plating solution to penetrate into even the deep depth or interior of, for instance, such long and narrow contact holes having such a high aspect ratio. Accordingly, this makes the formation of copper distributing wires from such a plating solution, quite difficult.

For this reason, there has been investigated, under the existing circumstances, a method which makes use of a gas, represented by the CVD technique as a substitute for the plating technique, as a means for forming copper distributing wires.

In the copper distributing wire-forming process, which makes use of the CVD technique, however, the formation of the copper film is greatly affected by the surface characteristic properties of the material used for forming a primary coat and more specifically, the process suffers from various problems in that (1) it is difficult to form initial nuclei and it takes a long period of time to form such initial nuclei; and (2) the film is apt to undergo the so-called island-like growth. Accordingly, it would be quite difficult to form a continuous film by the use of the foregoing process. For this reason, when the hole diameter: φ is not more than 0.2 μm and the width of the groove is not more than 0.2 μm and when the aspect ratio of these holes and/or grooves is not less than 4, the filling of, for instance, a hole would be accompanied by the formation of voids and accordingly, it would in fact be difficult to completely fill such a hole or the like. Thus, any CVD technique cannot be used for filling holes or grooves each having a diameter of not more than 0.1 μm, whose filling by the plating technique becomes difficult and this would result in a serious problem in the future.

The process likewise suffers from a problem in that it is difficult to ensure any excellent adhesion between the copper-containing film formed through the CVD technique and a barrier layer or the like.

The formation of a continuous film according to the CVD technique requires the acceleration of the nuclei-forming rate at the initial step of a film-forming process and an increase of the density of nuclei thus formed and accordingly, the role of a barrier layer (adherent layer) used as the primary coat would become quite important. At the same time, it is likewise important to ensure good adhesion between the barrier layer (adherent layer) and the copper-containing film for the formation of copper distributing wires.

When using a copper film formed according to the CVD technique as distributing wires, there has been known a method which comprises the steps of forming, in advance, a vanadium nitride film according to the reactive sputtering technique or the CVD technique and then growing a film of a copper material on the vanadium nitride film by the CVD technique to thus form a barrier layer having good adhesion to the copper film and having a small internal stress (see, for instance, Patent Document 1 specified later). In this case, bis(cyclopenta-dienyl) vanadium(III) is, for instance, used as a raw material for forming a barrier layer, but any satisfactory barrier layer has not always been prepared. Moreover, there has been used known materials such as (hexafluoro-acetyl acetonato) copper(I) trimethyl vinyl silane [Cu(hfac)(tmvs)] as the raw materials for forming copper-containing films, but the hole is not always completely filled therewith when the diameter of the hole is small, under the existing circumstances. This would possibly be resulted from the characteristic properties of the primary coat.

The conventionally used Cu(hfac)(tmvs) described above suffers from additional problems such that any desired copper-containing film cannot be prepared in good reproducibility (any stable filling of, for instance, holes cannot be ensured when the size of the opening of the hole: φ is not more than 0.2 μm and when the aspect ratio is not less than 4), which would possibly be resulted from the characteristic properties of the primary coat, and that voids are generated due to the annealing treatment after the step of filling the holes or the like.

FIGS. 6 and 7 schematically show voids possibly generated when a copper-containing film is formed according to the conventional techniques. More specifically, FIG. 6 shows the voids generated when copper distributing wires are formed by applying a conventional copper-containing film on a conventional barrier layer to thus fill holes or the like present thereon with the same, while FIG. 7 illustrates the conditions of voids generated during the annealing treatment carried out after the conventional step of forming copper distributing wires.

When forming copper distributing wires, the foregoing problems would arise and accordingly, the conventional techniques would never produce any LSI element provided with highly reliable distributing wires. Thus, one of the causes for this would be believed to be the instability of the raw materials typical of the Cu(hfac)(tmvs) complex described above and for this reason, there has been desired for the development of a raw material for forming copper-containing film, which is excellent in hole- or groove-filling properties and which can satisfy other characteristic properties as well.

Moreover, there have likewise been known special copper complexes as raw materials for forming copper-containing films according to the CVD technique (see, for instance, Patent Document 2 specified below). When using the copper complex, however, there are many problems remaining unsolved. For instance, any condition required for forming a desired copper-containing film has not yet been elucidated.

Patent Document 1: Japanese Un-Examined Patent Publication 2003-17437 (Claims);
Patent Document 2: Japanese Un-Examined Patent Publication 2003-292495 (Claims).

DISCLOSURE OF THE INVENTION

Problems that the Invention is to Solve

Accordingly, it is an object of the present invention to solve the foregoing problems associated with the conventional techniques and more specifically, to provide a method for forming copper distributing wires which comprises the steps of forming a primary coat consisting of a vanadium- or titanium-containing film having excellent characteristic properties (for instance, it may ensure excellent hole- or groove-filling properties of a copper-containing film formed in the subsequent step and it can ensure good adhesion between the primary coat and the copper-containing film) according to the CVD technique as a barrier layer and/or an adherent layer; and subsequently forming such a copper-containing film having excellent properties on the primary coat likewise according to the CVD technique.

Means for the Solution of the Problems

The copper distributing wire-forming method according to the present invention comprises the steps of forming a primary coat consisting of a vanadium- or titanium-containing film on a subject or substrate on which a film is to be formed, the film carrying holes and/or grooves formed thereon in advance, according to the CVD technique while using a raw gas consisting of a tetravalent amide-type vanadium-containing organometal compound or a tetravalent amide-type titanium-containing organometal compound as well as a reducing gas; and then forming a copper-containing film thereon by the CVD technique to thus fill the holes and/or grooves with the copper-containing film.

The foregoing tetravalent amide-type vanadium-containing organometal compound as a raw material is preferably tetrakis-diethyl-amino vanadium (TDEAV), tetrakis-dimethyl-amino vanadium (TDMAV) or tetrakis-ethylmethyl-amino vanadium; and the foregoing tetravalent amide-type titanium-containing organometal compound is preferably tetrakis-diethyl-amino titanium (TDEAT), tetrakis-dimethyl-amino titanium (TDMAT) or tetrakis-ethylmethyl-amino titanium.

The foregoing reducing gas is preferably one capable of generating H* radicals or H$^+$ ions through decomposition or dissociation.

The foregoing reducing gas is preferably a gas selected from the group consisting of hydrazine derivatives, $NH_3$, $H_2$, $SiH_4$ and $Si_2H_6$.

The hydrazine derivative is preferably hydrazine in which one or two hydrogen atoms thereof are substituted with a substituent selected from the group consisting of methyl group, ethyl group and linear or branched butyl group. In this respect, the substituents may be the same or different. Moreover, the hydrazine derivative is more preferably tertiary butyl hydrazine (TBH).

The foregoing tetravalent amide-type vanadium- or titanium-containing organometal compound is preferably reacted with a reducing gas specified above at a temperature falling within the range in which the film-forming rate may vary depending on the temperature of the subject on which a desired film is to be formed (film-forming subject) to thus form a vanadium- or titanium-containing film.

According to the present invention, when the aforementioned copper-containing film is formed on the primary coat prepared by the reaction of the foregoing organometal raw gas with the reducing gas, the copper-containing film is formed, according to the CVD technique, while using a copper complex represented by the following general formula (I) (in the formula (I), X, Y and Z are the same as those specified below) which possesses, as a ligand, a β-diketonate group represented by the following general formula (I)' (in the formula (I)', Z represents a hydrogen atom or an alkyl group having 1 to 4 carbon atoms; X represents a group denoted by the following general formula (I-I) (in the formula (I-I), $R^a$ represents a linear or branched alkylene group having 1 to 5 carbon atoms, and $R^b$, $R^c$ and $R^d$ each independently represent a linear or branched alkyl group having 1 to 5 carbon atoms), Y represents a group denoted by the following general formula (I-I) (in the formula (I-I), $R^a$ represents a linear or branched alkylene group having 1 to 5 carbon atoms, and $R^b$, $R^c$ and $R^d$ each independently represent a linear or branched alkyl group having 1 to 5 carbon atoms) or a linear or branched alkyl group having 1 to 8 carbon atoms):

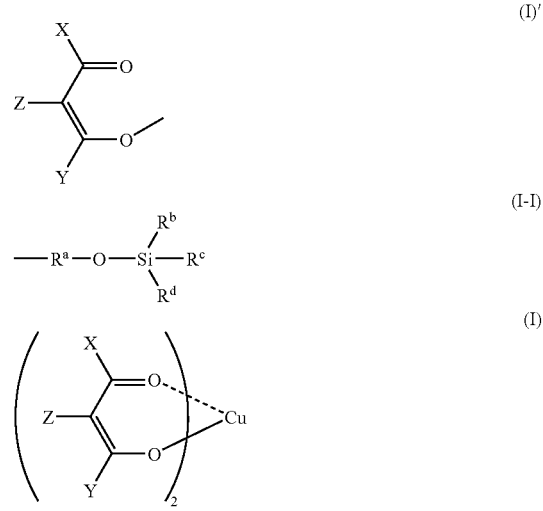

According to the present invention, it is also possible to use a gas consisting of a copper complex represented by the foregoing general formula (I), whose β-diketonate group, as a ligand thereof, represented by the foregoing general formula (I)' is one in which Z represents a hydrogen atom or an alkyl group having 1 to 4 carbon atoms; and X and Y, which may be the same or different from one another, each represent a linear or branched alkyl group having 1 to 8 carbon atoms or a $C_{1-8}$ alkyl group in which at most 9 hydrogen atoms thereof may be substituted with fluorine atoms (in Formula (I), the substituents X, Y and Z are the same as those defined above).

Alternatively, it is also possible to use a gas consisting of a copper complex represented by the foregoing general formula (I), whose β-diketonate group, as a ligand thereof, represented by the foregoing general formula (I)' is one in which Z represents a hydrogen atom or an alkyl group having 1 to 4 carbon atoms; and X and Y, which may be the same or different from one another, each represent a group denoted by the formula: $C_nH_{2n}$—O—$C_mH_{2m+1}$ (in the formula, n ranges from 1 to 8; m ranges from 0 to 7, provided that n+m is equal to or smaller than 8) or the foregoing group denoted by the formula: $C_nH_{2n}$—O—$C_mH_{2m+1}$ in which at most 9 hydrogen atoms thereof may be substituted with fluorine atoms (in Formula (I), the substituents X, Y and Z are the same as those defined above).

Furthermore, it is likewise possible to use a gas consisting of a copper complex represented by the foregoing general formula (I), whose β-diketonate group, as a ligand thereof, represented by the foregoing general formula (I)' is one in which Z represents a hydrogen atom or an alkyl group having 1 to 4 carbon atoms; and X and Y, which may be the same or different from one another, each represent a group denoted by the formula: $C_nH_{2n}$—CH=CH—$C_mH_{2m+1}$ (in the formula, n ranges from 0 to 6; m ranges from 0 to 6, provided that n+m is equal to or smaller than 6) or the foregoing group denoted by the formula: $C_nH_{2n}$—CH=CH—$C_mH_{2m+1}$ in which at most 9 hydrogen atoms thereof may be substituted with fluorine atoms (in Formula (I), the substituents X, Y and Z are the same as those defined above).

According to the present invention, the amount of the foregoing copper complex represented by Formula (I) to be supplied is preferably one which can satisfy the following relation as expressed in terms of the amount thereof per unit area of the film-forming surface on a film-forming subject:

$$8.0\times10^{-1}\text{cc/min·cm}^2 (3.6\times10^{-5}\text{mol/min·cm}^2) \geqq (\text{Amount to be Supplied}) \geqq 3.6\times10^{-3}\text{cc/min·cm}^2 (1.6\times10^{-7}\text{mol/min·cm}^2)$$

In this connection, if the amount thereof to be supplied is beyond the upper and lower limits specified above, it is not possible to ensure any desired excellent hole- and/or groove-filling properties of the present invention.

According to the method of the present invention, the film-forming temperature preferably ranges from 150 to 350° C. when forming a copper-containing film using the copper complex represented by the foregoing general formula (I) according to the CVD technique. If the film-forming temperature is less than 150° C., it takes a long period of time to ensure a desired amount of a film thus formed and accordingly, the use of such a temperature is impractical. On the other hand, it is not preferred to use a film-forming temperature of higher than 350° C., since the resulting film has an unacceptably high specific resistance.

When forming the foregoing copper-containing film, it is preferred to use a hydrogen atom-containing gas as the reducing gas. The hydrogen atom-containing gas preferably used herein is one selected from the group consisting of $NH_3$, $H_2$, $SiH_4$, $Si_2H_6$ and hydrazine derivatives (the hydrazine derivative is a hydrazine, one or two hydrogen atoms of which are substituted with a member selected from the group consisting of methyl group, ethyl group and linear or branched butyl group and these substituents may be the same or different from one another). In this respect, particularly preferably used herein is $H_2$ gas among others.

Effects of the Invention

According to the present invention, a primary coat possessing an excellent step-covering ability is formed in advance when a copper-containing film is deposited by the CVD technique, as has been described above. This would permit the achievement of such an effect that holes and/or grooves (including the side walls of these holes and/or grooves), such as those each having an opening (φ) of 0.05 μm) each having a high aspect ratio (for instance, 17), are completely filled with a uniform copper-containing film without accompanying the formation of any void.

As has been discussed above, the present invention makes use, as a primary coat, of a barrier layer which can prevent any mutual diffusion of the wire material and the insulating material and/or an adherent later which can prevent any peeling of films at the boundary between the layers of the wire material and the insulating material, whereby the method of the present invention shows an effect such that it becomes possible to efficiently form a copper-containing film useful as a material for forming desired copper distributing wires. In addition, the method of the present invention also shows an effect such that the easy formation of initial nuclei at a high nuclear density required for forming a desired copper-containing film within a very short period of time and the formation of a continuous film, as well as the use of a barrier layer and/or an adherent layer which can ensure the desired excellent adhesion between the copper-containing film thus formed and the barrier and/or adherent layers as a primary coat would likewise permit the efficient formation of a copper-containing film useful as a material for forming desired copper distributing wires.

BEST MODE FOR CARRYING OUT THE INVENTION

First, the structure of an embodiment of a CVD apparatus used for practicing the copper distributing wire-forming method according to the present invention will be described below in detail with reference to the accompanying drawings. The CVD apparatus can likewise be used for forming a barrier layer or an adherent layer serving as a primary coat for copper-containing film or copper distributing wires and therefore, the apparatus will be described below while taking, by way of example, the copper distributing wire-forming method according to the present invention which comprises the following both steps of forming the barrier or adherent layer and of forming the copper-containing film.

The CVD apparatus as shown in FIG. 1 is composed of a gas-supply device 1 for supplying, to the CVD apparatus, a carrier gas (such as $N_2$, Ar or He) and a reducing gas (such as $NH_3$ or $H_2$); a raw material-supply device 2 for supplying film-forming materials; a reaction device 3 for forming a metal-containing film; and an exhaust device 4 for discharging the raw material and the gases.

The gas-supply device 1 has such a function that it can transport the carrier gas and the reducing gas from the gas sources of these respective gases to the reaction device 3 through mass flow-controllers (such as MFC1 and MFC2 shown in the accompanying drawings) and pipe arrangement, while controlling the flow rate of each gas.

The raw material-supply device 2 has such a function that it can transport the raw material 202 included in a container 201 thereof to a reaction chamber 301 of the reaction device 3, while controlling the flow rate and pressure of the raw material to be supplied to the chamber. Referring now to FIG. 1, this raw material-supply device can be used for supplying a raw material which is in a liquid or solid state at ordinary temperature and accordingly, the device is used for converting, into a gas, a copper-containing film-forming raw material; a vanadium-containing film-forming organometal material such as TDEAV or TDMAV; a titanium-containing film-forming organometal material such as TDEAT or TDMAT; a reducing gas material, for instance, a hydrazine derivative (such as tertiary butyl hydrazine (TBH)) through a vaporizer 203 and introducing the gas into the reaction device 3. One of the basic structures of the raw material-supply device as shown in FIG. 1 is so designed that the gas such as the gaseous raw material can be transported to the reaction chamber 301 while controlling the flow rate and/or the pressure thereof supplied through the mass flow-controllers (such as L-MFC and MFC3 as shown in FIG. 1) and a pressure gage (such as 204 and 205 in FIG. 1). The piping work for transporting a raw material starting from the container 201 for accommodating a raw material to a shower plate 302 of the reaction device 3 and respective component parts such as valves are all subjected to a desired temperature-controlling treatment. In this respect, the temperature thereof is preferably controlled in such a manner that it falls within the range of from room temperature to about 270° C. Thus, the temperature of these parts can be controlled so that the gaseous raw material is never converted into a liquid to thus undergo any separation or deposition within them.

The reaction device 3 is composed of a shower plate 302 for appropriately supplying, to the surface of a substrate S, gaseous materials such as a gaseous raw material, a reducing gas and a carrier gas supplied from the raw material-supply device 2, and gaseous materials such as a carrier gas and a reducing gas supplied from the gas-supply device 1; a reaction chamber 301 capable of holding a desired film-forming atmosphere in the proximity of the substrate S; a substrate-placing table 303 capable of being heated (this is equipped with a heating means, although any such means is not shown in the figure); a gate valve 304 for isolating the atmosphere within the reaction chamber from, for instance, the neighboring substrate-transporting chamber; and a pressure gage 305 for monitoring the pressure of the film-forming atmosphere within the reaction chamber. The shower plate 302 is prepared from, for instance, a metal (such as stainless steel, Al, an Al alloy, Hastelloy (registered trade mark), or Inconel (available from INCO Company, Canada)) and the temperature thereof is preferably controlled in such a manner that it falls within the range of from room temperature to 250° C. The reaction chamber 301 is prepared from a metal (such as stainless steel, Al, an Al alloy, Hastelloy or Inconel) and the temperature thereof is likewise preferably controlled in such a manner that it falls within the range of from room temperature to 250° C. The substrate-placing table 303 can be prepared using a metal (such as stainless steel, Al, an Al alloy, Hastelloy or Inconel) or a ceramic material (such as $Al_2O_3$, AlN, SiN, SiC, or $SiO_2$). Preferably used herein is a substrate-placing table made of a ceramic material and the table is preferably prepared using AlN, among others, since it has a high thermal conductivity and it also shows a good temperature distribution even at a high temperature. The substrate-placing table 303 made of AlN can withstand the heat treatment carried out at a temperature ranging from room temperature to 600° C. The gate valve 304 is prepared using, for instance, a metal (such as stainless steel, Al, an Al alloy, Hastelloy or Inconel), and it is equipped with temperature monitors and heating means such as heaters in the interior and/or on the exterior of the same so that the temperature thereof can be controlled to a level ranging from room temperature to 250° C. The pressure gage 305 used herein should be one capable of withstanding a high temperature.

The exhaust device 4 is a device for adjusting the atmosphere within the reaction chamber 301. As shown in FIG. 1, the basic structure thereof comprises piping work, an exhaust valve 401, a pressure-control valve 402, a trap 403 for raw materials and a vacuum pump 404. The temperature of the respective parts distributed or arranged between the reaction chamber 301 and the vacuum pump 404 are all controlled to a desired level preferably ranging from room temperature to 250° C. The pressure-control valve 402 can be opened or closed so that the pressure within the chamber may be set at an arbitrary level in response to the pressure gage 305 arranged in the reaction chamber 301, on the basis of the value thereof. In addition, the piping work 5 is provided for transporting the gaseous raw material leaving the raw material-supply device 2 to the trap 403 for raw materials of the exhaust device 4 and accordingly, the gaseous raw material can stably be supplied to the reaction chamber 301 by switching the passage for transporting the raw gas toward the side of the reaction chamber 301 at an instance when the flow rate or supplied amount of the gaseous raw material discharged from the raw material-supply device 2 is stabilized. Moreover, when the supply of the gaseous raw material is completed or when the desired film-forming reaction is completed, the supply of the gaseous raw material to the reaction chamber 301 can immediately be terminated by switching the passage for transporting the raw gas toward the side of the piping work 5 to thus guide the gaseous raw material to the trap 403. This trap 403 for raw materials is a device having such a function that it can recover the gaseous raw material discharged from, for instance, the reaction chamber and it is quite effective for reducing the load (any clogging within the pump) applied to the vacuum pump 404 and for the reuse of the gaseous raw material. To improve the exhaustion power of the vacuum pump 404 as shown in FIG. 1, a secondary vacuum pump may be positioned between the pressure-control valve 402 and the vacuum pump 404.

The foregoing raw material-supply device usable in the present invention may likewise have a structure such as those shown in FIGS. 2 to 4 in addition to that depicted in FIG. 1. Either of these structures including that as shown in FIG. 1 is so designed that the gaseous raw material can be transported to the reaction chamber 301 while controlling the flow rate and/or pressure thereof supplied through the mass flow-controllers (such as L-MFC, MFC3 and MFC4 as shown in FIGS. 2 to 4) and pressure gages (such as 204 and 205 as shown in FIGS. 2 to 4). In this connection, any vaporizer is not shown in the accompanying figures, but the device usable in the present invention may, if necessary, be provided with a vaporizer.

The raw material-supply device 2 as shown in FIG. 2 has such a structure that the gaseous raw material 202 contained in the container 201 for accommodating the raw material can be transported to the reaction chamber 301 through a mass flow controller (L-MFC) by the action of a pressurized gas (such as $N_2$, Ar or He) supplied at a predetermined pressure. Similarly, the raw material-supply device 2 as shown in FIG. 3 has such a structure that the gaseous raw material 202 contained in the container 201 for accommodating the raw material can be transported to the reaction chamber 301 through a mass flow controller (MFC3) simultaneous with a carrier gas and a reducing gas supplied at a desired pressure. In addition, the raw material-supply device 2 as shown in FIG. 4 has such a structure that the gaseous raw material 202 contained in the container 201 for accommodating the raw material can be transported to the reaction chamber 301 through a mass flow controller (MFC4).

According to the present invention, a barrier layer and/or an adherent layer is formed on the surface of a substrate prior to the formation of an intended copper-containing film and in this connection, metallic raw materials capable of being used in the formation of such barrier and/or adherent layers are preferably tetravalent amide-type vanadium-containing or titanium-containing organometallic raw materials and specific examples include $V[NR^1R^2]_4$, $V[NR^1R^2]_3.Cl$, $V[NR^1R^2]_2.Cl_2$ and $V[NR^1R^2].Cl_3$; and $Ti[NR^1R^2]_4$, $Ti[NR^1R^2]_3.Cl$, $Ti[NR^1R^2]_2.Cl_2$ and $Ti[NR^1R^2].Cl_3$, wherein $R^1$ and $R^2$ may be the same or different from one another and each represents a member selected from the group consisting of, for instance, $C_nH_{2n+1}$ (n is an integer ranging from 0 to 4), $C_mH_{2m}O$ (m is an integer ranging from 0 to 4), $CH_2OH$ and phenyl groups. Cl may be replaced with a halogen atom other than Cl. More preferably used herein are TDEAV, TDMAV, TDEAT and TDMAT listed above, among the foregoing metallic raw materials.

The foregoing reducing gases usable herein include, for instance, those capable of generating H* radicals or $H^+$ ions through decomposition or dissociation and examples thereof are hydrazine derivatives (such as tertiary butyl hydrazine (TBH): $(CH_3)_3CNHNH_2$), $NH_3$, $H_2$ and $SiH_4$. It is also possible to use other hydrazine derivatives (such as those in which one or two hydrogen atoms thereof are substituted with a substituent selected from the group consisting of alkyl groups such as methyl, ethyl and linear or branched butyl groups). Among these reducing gases, preferably used herein are gases (such as TBH and $NH_3$) which can react with TDEAV or TDEAT gas and can accelerate the nitrification in the step for forming a vanadium-containing film or a titanium-containing film.

As the carrier gases, usable herein are, for instance, rare gases such as argon and helium; and inert gases such as $N_2$.

Next, an example of the copper complex usable in the present invention will hereunder be described in more detail.

Specific examples of silyl ether-containing β-diketone compounds which are used as ligands of this copper complex and which can provide copper β-diketonate complexes may be, for instance, those represented by the following structural formulas (III)' to (XIV)':

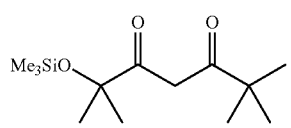
(III)'

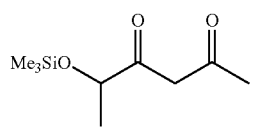
(IV)'

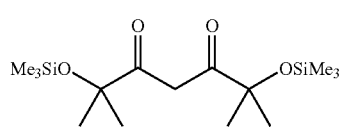
(V)'

-continued

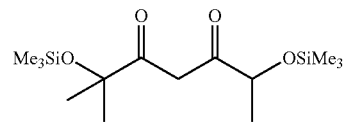
(VI)'

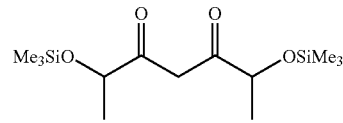
(VII)'

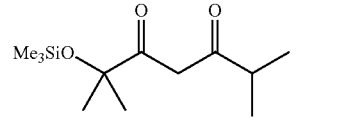
(VIII)'

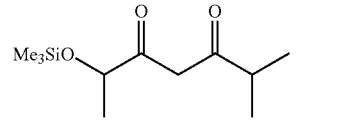
(IX)'

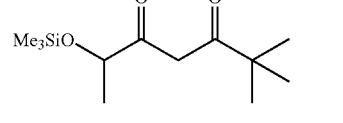
(X)'

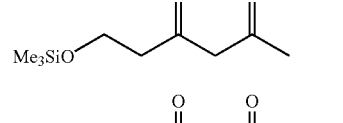
(XI)'

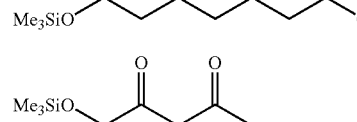
(XII)'

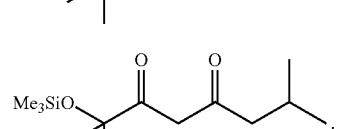
(XIII)'

(XIV)'

These β-diketone compounds can be prepared according to any known method (such as that disclosed in Japanese Un-Examined Patent Publication 2003-292495).

The copper β-diketonate complex or a copper complex having enolate anions of β-diketone as ligands thereof can be prepared by, for instance, the reaction of the foregoing β-diketone with copper hydroxide (copper complex synthesis method 1 specified below). A solvent is used in the synthesis and usable herein include almost all of the organic solvents, for instance, hydrocarbons such as hexane and toluene; ethers such as THF and dimethoxy ethane; nitrites such as acetonitrile; halogenated hydrocarbons such as dichloromethane; alcohols such as isopropanol; and esters such as ethyl acetate. The water generated through the reaction in the synthesis method 1 may be removed from the reaction system by, for instance, a method which makes use of the azeotropic distillation thereof together with the reaction solvent such as toluene; a method in which the water is removed through the evaporation at room temperature under a reduced pressure together with the reaction solvent such as THF after the completion of the reaction; or by a method in which the reaction is carried out in the co-existence of a dehydrating agent such as anhydrous sodium sulfate, anhydrous magnesium sulfate, anhydrous copper sulfate, or molecular sieves, or a water-absorptive polymer (such as nonionic type ones) to thus remove the water generated during the reaction.

Complex-Synthesis Method 1:

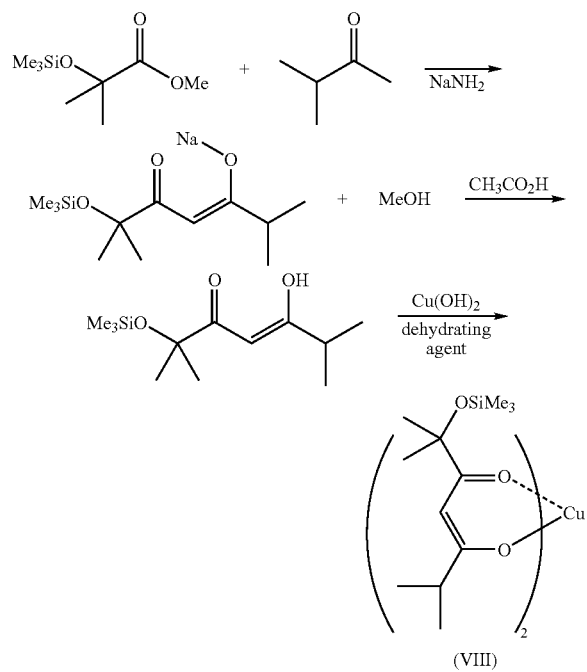

The compound represented by the following structural formula (VIII) is an example of the foregoing copper complex having silyl ether type β-diketonate ligands. This complex corresponds to the copper complex whose ligands are those derived from the compounds represented by the foregoing structural formula (VIII)', or the copper complex represented by the foregoing general formula (I) wherein X is a group: $(CH_3)_3SiO—C(CH_3)_2—$; Y is a group: $(CH_3)_2CH—$; and Z is H, or more specifically, a copper complex having enolate anions of β-diketone as ligands thereof; bis(2,6-dimethyl-2-(trimethyl-silyloxy)-3,5-heptanedionato) copper(II) complex; and $C_{24}H_{46}CuO_6Si_2$ (hereunder referred to as $Cu(SOPD)_2$ or SOPD):

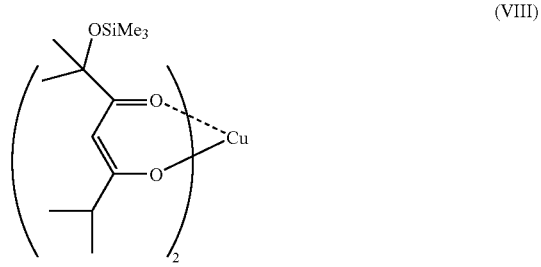

Each of the β-diketones represented by the foregoing structural formulas (III)' to (VII)' and the foregoing structural formulas (IX)' to (XIV)' may likewise provide each corresponding copper complex having enolate anions derived from each β-diketone as ligands thereof and having a structure similar to that represented by the foregoing structural formula (VIII).

Examples of copper complexes represented by the foregoing general formula (I) (provided that Z represents a hydrogen atom or an alkyl group having 1 to 4 carbon atoms; and X and Y, which may be the same or different from one another, each represent a linear or branched alkyl group having 1 to 8 carbon atoms or a $C_{1-8}$ alkyl group in which at most 9 hydrogen atoms thereof may be substituted with fluorine atoms) include bis(acetylacetonato) copper(II) complex, bis(2,6-dimethyl-3,5-heptanedionato) copper(II) complex, bis(dipivaloyl-methanato) copper(II) complex or bis(2,2,6,6-tetramethyl-3,5-heptanedionato) copper(II) complex, bis(6-ethyl-2,2-dimethyl-3,5-decanedionato) copper(II) complex, and bis(hexafluoro-acetyl-acetonato) copper(II) complex.

Examples of copper complexes represented by the foregoing general formula (I) (provided that Z represents a hydrogen atom or an alkyl group having 1 to 4 carbon atoms; and X and Y, which may be the same or different from one another, each represent a group denoted by the formula: $C_nH_{2n}—O—C_mH_{2m+1}$ (in the formula, n ranges from 1 to 8; m ranges from 0 to 7, and n and m satisfy the relation: n+m≦8) or the foregoing group denoted by the formula: $C_nH_{2n}—O—C_mH_{2m+1}$ in which at most 9 hydrogen atoms thereof may be substituted with fluorine atoms) include bis(1-ethoxy-5,5-dimethyl-2,4-hexanedionato) copper(II) complex, bis(1-ethoxy-5-methoxy-2,4-pentanedionato) copper(II) complex, and bis(1-trifluoromethoxy-5,5-dimethyl-2,4-hexanedionato) copper(II) complex.

Examples of copper complexes represented by the foregoing general formula (I) (provided that Z represents a hydrogen atom or an alkyl group having 1 to 4 carbon atoms; and X and Y, which may be the same or different from one another, each represent a group denoted by the formula: $C_nH_{2n}—CH=CH—C_mH_{2m+1}$ (in the formula, n ranges from 0 to 6; m ranges from 0 to 6, and n and m satisfy the relation: n+m≦6) or the foregoing group denoted by the formula: $C_nH_{2n}—CH=CH—C_mH_{2m+1}$ in which at most 9 hydrogen atoms thereof may be substituted with fluorine atoms) include bis(2,2-dimethyl-6-heptaene-3,5-dionato) copper(II) complex, bis(1,7-decene-4,6-dionato) copper(II) complex, and bis(1,1,1-trifluoro-5-hexene-2,4-dionato) copper(II) complex.

As a vaporization method used in the formation of a copper-containing film using the foregoing copper complex according to the CVD method (ordinary pressure or low or reduced pressure CVD technique), usable herein include, for instance, a method in which the copper complex per se is directly vaporized in the vaporizer; and a method which comprises the steps of diluting the copper complex with a solvent such as hexane, octane, toluene, cyclohexane, methyl cyclohexane, ethyl cyclohexane or tetrahydrofuran and then transporting the resulting solution of the copper complex to the vaporizer to thus vaporize the complex within the device. In addition, the copper complex can be vapor-deposited on the surface of a substrate according to any known CVD technique. In addition to such a method in which a copper layer is deposited through the simple thermal decomposition of such a copper complex under a reduced pressure or in the co-existence of an inert gas, usable herein also include, for instance, a method in which metal copper is deposited on the surface of a substrate, according to the plasma CVD technique, carried out in the co-existence of a reducing gas such as hydrogen gas and the copper complex or in the presence of hydrogen gas. Furthermore, it is also possible to form a copper oxide film through the vapor-deposition according to the thermal decomposition of the copper complex in the presence of oxygen gas or according to the plasma CVD technique in the presence of oxygen gas.

The film-forming subjects usable in the present invention are not restricted to specific ones insofar as they are substrate used for preparing semiconductor elements and, for instance, $SiO_2/Si$ substrates carrying holes and/or grooves formed thereon are used in the following Examples, but Low-k substrates may likewise be employed in the present invention. Examples of such Low-k substrates include SiOC type ones (such as those available from AMAT Company under the trade name of Black Diamond; those available from Novellus Company under the trade name of Coral; those available from ASM Company under the trade name of Aurola; those available from TRIKON Company under the trade name of Orion; those available from Dow Chemical Company under the trade name of SiLK; those available from Honeywell Electric Materials Company under the trade name of FLARE; SiOF; HSQ; MSQ; and NCS (Nano Crystal Silica available from Fujitsu Ltd.)).

The present invention will hereunder be described with reference to the following Examples in which the method of the present invention is carried out using the aforementioned CVD apparatus. More specifically, the following are detailed description of the film-forming process according to the present invention, which comprises the steps of forming a vanadium- or titanium-containing film as a barrier layer, forming a copper-containing film on the barrier layer and then forming the copper-containing film into copper distributing wires.

Example 1

In this Example, a barrier layer consisting of vanadium nitride was formed while variously changing the barrier layer-forming conditions and then a copper-containing film was deposited on the barrier layer to thus variously investigate the initial nucleation conditions.

Step 1:

A vanadium-containing film was formed on the surface of a substrate S using the CVD apparatus as shown in FIG. 1. In this respect, the substrate S used herein was a wafer ($SiO_2/Si$) having a diameter of 8 inches, on which a silicon oxide film had been formed.

The gate valve 304 of the reaction device 3 was opened and then the substrate S was conveyed into the reaction chamber 301 using a robot positioned in the chamber in the proximity of the reaction chamber. The conveyance of the substrate is desirably carried out in a vacuum for the prevention of any adhesion, onto the surface of the substrate, of gases present in the air, for instance, carbon atom-containing gases (such as CO or $CO_2$), oxygen-containing gases (such as $O_2$), and water ($H_2O$) or for the prevention of any diffusion or penetration of these gases into the interior of the substrate. Accordingly, the substrate was conveyed into the reaction chamber under vacuum conditions, in this Example.

The substrate S conveyed into the reaction chamber 301 was placed on a substrate-placing table 303 positioned within the reaction chamber and provided with a heating means in such a manner that the principal face or the surface of the substrate S faced the shower plate 302, while the back face thereof faced the side of the substrate-placing table. This substrate-placing table was always maintained at a predetermined film-forming temperature.

Then $N_2$ gas discharged from the gas-supply device 1 was introduced into the reaction chamber 301 through the mass flow controller MFC1 while controlling the flow rate thereof to 1500 sccm and the substrate-placing table was heated so that the temperature of the substrate was set at 350° C., while maintaining the reaction chamber at a desired film-forming pressure. After the elapse of a time ranging from 0 to 10 minutes, the film-forming operation was initiated according to the film-forming conditions 1 to 4 specified below. As the raw materials, there were used TDEAV (tetrakis-diethylamino vanadium: $V[N(C_2H_5)_2]_4$) and TDMAV (tetrakis-dimethylamino vanadium: $V[N(CH_3)_2]_4$). In this connection, the film-forming operations under the film-forming conditions 2 and 4 were carried out after forming respective films according to the film-forming conditions 1 and 3, respectively. More specifically, the operations under the conditions 2 and 4 comprise the steps of terminating the supply of a metal raw material, the carrier for the metal raw material and the reducing gas after forming the respective films according to the film-forming conditions 1 and 3, allowing only the carrier gas ($N_2$ gas) to flow through the reaction chamber at a flow rate of 1500 sccm to thus purge the reaction chamber for one minute and then carrying out the film-forming operation to improve or modify the quality of the film surface. Thus, there were obtained the substrates with the improved or modified film surface.

In the Case where TDEAV was Used as Raw Material:
VN Film-Forming Conditions 1:
  Amount of Supplied TDEAV: 84 mg/min;
  Flow Rate of Carrier for TDEAV, $N_2$: 400 sccm;
  Flow Rate of TBH: 80 sccm ($NH_3$ flow rate: 13 sccm; $H_2$ flow rate: 1680 sccm);
  Flow Rate of Carrier, $N_2$: 1500 sccm;
  Film-Forming Pressure: 340 Pa;
  Film-Forming Time: 5 minutes;
  Film-Forming Temperature: 350° C.
  Film Thickness: 20 nm
VN Film-Forming Conditions 2:
  Amount of Supplied TDEAV: 84 mg/min;
  Flow Rate of Carrier for TDEAV, $N_2$: 400 sccm;
  Flow Rate of Carrier, $N_2$: 1580 sccm;
  Film-Forming Pressure: 340 Pa;
  Film-Forming Time: 5 minutes;
  Film-Forming Temperature: 350° C.;
  Film Thickness: 25 nm The electrical resistivity of each vanadium-containing film prepared according to the method using the film-forming conditions 1 specified above was found to fall within the range of from 2500 to 3000 Ω·cm, while the electrical resistivity of each vanadium-containing film prepared according to the method using the film-forming conditions 2 specified above was found to fall within the range of from 1200 to 1500Ω·cm. The vanadium-containing films prepared using the film-forming conditions 1 and 2 specified above were inspected for the compositions thereof by the XPS technique. The results thus obtained are summarized in the following Table 1.

TABLE 1

| Raw Material | V (%) | N (%) | C (%) | O (%) |
|---|---|---|---|---|
| TDEAV | 42 | 13 | 41 | 4 |
| TDEAV + $NH_3$ | 48 | 19 | 30 | 3 |
| TDEAV + TBH | 51 | 25 | 19 | 5 |
| TDEAV + $H_2$ | 43 | 15 | 38 | 4 |

As will be clear from the data listed in the foregoing Table 1, the contents of vanadium and nitrogen present in the resulting film prepared using a reducing gas were found to be higher than those observed for the film prepared in the absence of any reducing gas and it was found that the nitrification of the resulting film was accelerated, in particular, when using $NH_3$ or TBH as the reducing gas.

In the Case where TDMAV was Used as Raw Material:

VN Film-Forming Conditions 3:
  Amount of Supplied TDMAV: 84 mg/min;
  Flow Rate of Carrier for TDMAV, $N_2$: 400 sccm;
  Flow Rate of TBH: 80 sccm ($NH_3$ flow rate: 13 sccm; $H_2$ flow rate: 1680 sccm);
  Flow Rate of Carrier, $N_2$: 1580 sccm;
  Film-Forming Pressure: 340 Pa;
  Film-Forming Time: 5 minutes;
  Film-Forming Temperature: 300° C.
  Film Thickness: 25 nm VN Film-Forming Conditions 4:
  Film-Forming Pressure: 340 Pa;
  Film-Forming Time: 5 minutes;
  Amount of Supplied TDMAV: 84 mg/min;
  Flow Rate of Carrier for TDMAV, $N_2$: 400 sccm;
  Film-Forming Temperature: 300° C.;
  Flow Rate of Carrier, $N_2$: 1580 sccm;
  Film Thickness: 25 nm The electrical resistivity of each vanadium-containing film prepared according to the method using the film-forming conditions 3 specified above was found to fall within the range of from 1200 to 3000Ω·cm, while the electrical resistivity of each vanadium-containing film prepared according to the method using the film-forming conditions 4 specified above was found to fall within the range of from 1000 to 1500Ω·cm. The vanadium-containing films prepared using the film-forming conditions 1 and 2 specified above were inspected for the compositions thereof by the XPS technique. The results thus obtained are summarized in the following Table 2.

TABLE 2

| Raw Material | V (%) | N (%) | C (%) | O (%) |
|---|---|---|---|---|
| TDMAV | 50 | 20 | 24 | 6 |
| TDMAV + $NH_3$ | 51 | 27 | 14 | 8 |
| TDMAV + TBH | 49 | 25 | 10 | 16 |
| TDMAV + $H_2$ | 50 | 21 | 23 | 6 |

As will be clear from the data listed in the foregoing Table 2, the contents of vanadium present in the films prepared in the presence and absence of a reducing gas were almost identical to one another, but the film prepared using a reducing gas had a nitrogen content higher than that observed for the film prepared in the absence of any reducing gas. This clearly indicates that the nitrification of the resulting film can be accelerated, in particular, when using $NH_3$ or TBH as the reducing gas.

By way of comparison, a TaN film as a barrier layer was formed on the surface of a substrate by the sputtering technique under the following film-forming conditions.

TaN Film-Forming Conditions:
  Substrate: $SiO_2$/Si;
  Film-Forming Pressure: $3 \times 10^{-2}$ Pa;
  Electric Power: 15 kW;
  Ratio of Supplied Gases: Ar: $N_2$=6:15;
  Film-Forming Temperature: 160° C.;
  Film Thickness: 20 nm Step 2:

The following are the detailed description of this step 2, in which a copper-containing film is deposited on the barrier layer formed according to the foregoing step 1.

The following film-forming processes were carried out using the CVD apparatus as shown in FIG. 1. The substrate provided thereon with the vanadium-containing film formed in the foregoing step 1 was conveyed to a copper-containing film-forming reaction chamber through a transportation chamber (maintained at a vacuum) arranged in the vicinity of the reaction chamber 301, while paying much attention not to expose the substrate to the air for the prevention of any oxidation of the surface thereof, followed by placing the substrate on the substrate-placing table 303 maintained at a predetermined temperature. Separately, an $SiO_2$/Si substrate free of any vanadium-containing film was likewise placed on the substrate-placing table 303 of the copper-containing film-forming reaction chamber 301. To these substrates, there was supplied $H_2$ gas while controlling the flow rate thereof and then the substrates were heated up to a set temperature over a time ranging from 0 to 10 minutes while maintaining the reaction chamber 301 at a constant pressure. In this case, the pressure of the reaction chamber and the temperature of the substrates were set at the same levels used in the subsequent step for forming a copper-containing film. This $H_2$ gas also served to remove the oxide film possibly formed on the substrate surface. In this case, $H_2$ gas was used. However, it is also possible to use other gases which have a variety of characteristic properties such that they have a small molecular size, they are quite susceptible to diffusion and they have a high thermal conductivity, and which can release $H^*$ radicals or $H^+$ ions through decomposition or dissociation and specific examples of such gases usable herein include TBH, $NH_3$, $SiH_4$ and hydrazine derivatives.

Then a raw material for forming copper-containing films was supplied onto the surface of the substrates arranged within the reaction chamber 301 in a hydrogen gas atmosphere to thus form a copper-containing film on the substrate surface according to the film-forming method carried out under the following copper-containing film-forming conditions 1 to 3 and to simultaneously examine or evaluate the ability of forming initial nuclei and the adhesion between the barrier layer and the resulting copper-containing film. In this connection, the raw material was a solution obtained by dissolving 0.5 mole of a complex: $Cu(SOPD)_2$ in octane as a solvent to thus give one liter of an octane solution, which was sealed in a raw material container prior to the practical use thereof.

Copper-Containing Film-Forming Conditions 1:
Substrates Used
  (1) A substrate provided thereon with a barrier layer formed according to the VN film-forming conditions 1 in Step 1, while using TBH as a reducing gas at a flow rate of 80 sccm;
  (2) A substrate provided thereon with a barrier layer formed according to the VN film-forming conditions 1 in Step 1, while using $NH_3$ as a reducing gas at a flow rate of 13 sccm;
  (3) A substrate provided thereon with a barrier layer formed according to the VN film-forming conditions 1 in Step 1, while using $H_2$ as a reducing gas at a flow rate of 1680 sccm;
  (4) A substrate provided thereon with a barrier layer formed according to the VN film-forming conditions 2 in Step 1, without using any reducing gas;
  (5) A substrate provided thereon with a barrier layer formed according to the VN film-forming conditions 3 in Step 1, while using TBH as a reducing gas at a flow rate of 80 sccm;
  (6) A substrate provided thereon with a barrier layer formed according to the VN film-forming conditions 3 in Step 1, while using $NH_3$ as a reducing gas at a flow rate of 13 sccm;
  (7) A substrate provided thereon with a barrier layer formed according to the VN film-forming conditions 3 in Step 1, while using $H_2$ as a reducing gas at a flow rate of 1680 sccm;

(8) A substrate provided thereon with a barrier layer formed according to the VN film-forming conditions 4 in Step 1, without using any reducing gas;

(9) An SiO$_2$/Si substrate free of any barrier layer; and

(10) A substrate provided thereon with a barrier layer formed according to the TaN film-forming conditions in Step 1.

Film-Forming Pressure: 1780 Pa;
Film-Forming Time: One minute;
Amount of Supplied SOPD: 78 mg/min (3.15 cc/min);
Flow Rate of Carrier for SOPD, N$_2$: 400 sccm;
Film-Forming Temperature: 200 to 350° C.;
Flow Rate of H$_2$: 2500 sccm.

Each of the copper-containing films prepared according to the method described above was inspected for the formation of initial nuclei through the use of the SEM and AFM techniques. The results thus obtained are summarized in the following Table 3.

TABLE 3

| | Substrate Used | | | |
|---|---|---|---|---|
| | (9) | (10) | (1) to (3), (5) to (7) | (4), (8) |
| TDEAV Pretreatment | No | No | Step 1: Film-Forming Conditions 1 | Step 1: Film-Forming Conditions 2 |
| TDMAV Pretreatment | No | No | Step 1: Film-Forming Conditions 3 | Step 1: Film-Forming Conditions 4 |
| Copper-Containing Film-formation | X | X | ○ | ○ |

In Table 3, each open circle indicates that the initial nucleation could be confirmed, while each cross indicates that any initial nucleation could not be confirmed at all. The foregoing results clearly indicate that the pre-treatment of a substrate with TDEAV, TDMAV raw materials prior to the copper-containing film-formation would certainly permit the acceleration of the initial nucleation and the considerable increase of the nuclear density in the initial nucleation within a very short period of time.

Copper-Containing Film-Forming Conditions 2:
Substrate Used:

(1) A substrate provided thereon with a barrier layer formed according to the VN film-forming conditions 2 in Step 1, without using any reducing gas;

(2) A substrate provided thereon with a barrier layer formed according to the VN film-forming conditions 4 in Step 1, without using any reducing gas;

(3) An SiO$_2$/Si substrate free of any barrier layer; and (4) A substrate provided thereon with a barrier layer formed according to the TaN film-forming conditions in Step 1.

Film-Forming Pressure: 1780 Pa;
Film-Forming Time: 15 to 45 minutes;
Amount of Supplied SOPD: 78 mg/min (3.15 cc/min);
Flow Rate of Carrier for SOPD, N$_2$: 400 sccm;
Film-Forming Temperature: 200 to 350° C.;
Flow Rate of H$_2$: 2500 sccm.

The copper-containing films were found to have a thickness ranging from 40 to 260 nm. Each copper-containing film was then subjected to a tape test. In this tape test, nine Chinese characters (kanji) "田"(each kanji consisted of four squares having a size of 5 mm square) were cut on each of the copper-containing films thus prepared, with a diamond cutter, in the X-Y directions along the diameter of the substrate at equal spaces and an adhesive tape was attached to the surface of the substrate and then the adhesive tape was peeled off from the surface.

As a result, it was found that all of the copper-containing film samples formed on the VN barrier layer were not peeled off from the surface thereof when the film thickness was not more than 100 nm. In addition, it was also found that the samples of copper-containing films formed at a film-forming temperature ranging from 270 to 350° C. were never peeled off from the surface thereof even when the thickness thereof was at the highest 260 nm. Contrary to this, it was found that the copper-containing films having a thickness of not more than 100 nm were completely or partially peeled off from the surface of the substrate when each copper-containing film was directly applied onto the SiO$_2$ film surface. Similarly, when a TaN film was formed on the surface of an SiO$_2$/Si substrate by the sputtering technique and then a copper-containing film was deposited on the TaN film by the CVD technique, it was found that the copper-containing films having a thickness of not more than 100 nm were completely or partially peeled off from the surface of the substrate.

Copper-Containing Film-Forming Conditions 3:
Substrate Used:

(1) A substrate provided thereon with a barrier layer formed according to the VN film-forming conditions 1 in Step 1, while using TBH as a reducing gas at a flow rate of 80 sccm;

(2) A substrate provided thereon with a barrier layer formed according to the VN film-forming conditions 1 in Step 1, while using NH$_3$ as a reducing gas at a flow rate of 13 sccm;

(3) A substrate provided thereon with a barrier layer formed according to the VN film-forming conditions 1 in Step 1, while using H$_2$ as a reducing gas at a flow rate of 1680 sccm (in this case, any N$_2$ gas stream was not used);

(4) A substrate provided thereon with a barrier layer formed according to the VN film-forming conditions 3 in Step 1, while using TBH as a reducing gas at a flow rate of 80 sccm;

(5) A substrate provided thereon with a barrier layer formed according to the VN film-forming conditions 3 in Step 1, while using NH$_3$ as a reducing gas at a flow rate of 13 sccm;

(6) A substrate provided thereon with a barrier layer formed according to the VN film-forming conditions 3 in Step 1, while using H$_2$ as a reducing gas at a flow rate of 1680 sccm (in this case, any N$_2$ gas stream was not used);

(7) A substrate provided thereon with a barrier layer formed according to the TaN film-forming conditions in Step 1; and (8) An SiO$_2$/Si substrate free of any barrier layer.

Film-Forming Pressure: 1780 Pa;
Film-Forming Time: 15 to 45 minutes;
Amount of Supplied SOPD: 78 mg/min (3.15 cc/min);
Flow Rate of Carrier for SOPD, N$_2$: 400 sccm;
Film-Forming Temperature: 200 to 350° C.;
Flow Rate of H$_2$: 2500 sccm.

The copper-containing films were found to have a thickness ranging from 30 to 180 nm. Each copper-containing film was then subjected to a tape test according to the same method used above. In other words, nine Chinese characters (kanji) "田"(each kanji consisted of four squares having a size of 5 mm square) were cut on each of the copper-containing films thus prepared, with a diamond cutter, in the X-Y directions along the diameter of the substrate at equal spaces and an adhesive tape was attached to the surface of the substrate and then the adhesive tape was peeled off from the surface.

As a result, it was found that all of the copper-containing film samples formed on the VN barrier layer were not peeled off from the surface thereof when the film thickness was not more than 100 nm. In addition, it was also found that the samples of copper-containing films formed at a film-forming temperature ranging from 270 to 350° C. were never peeled off from the surface thereof even when the thickness thereof was at the highest 180 nm. Separately, copper-containing films were likewise prepared using TBH, $H_2$, or $NH_3$, as a reducing gas, but there was not observed any difference in the adhesion between each copper-containing film thus formed and the barrier layer. Contrary to this, it was found that the copper-containing films having a thickness of not more than 100 nm were completely or partially peeled off from the surface of the substrate when each copper-containing film was directly applied onto the $SiO_2$ film surface. Similarly, when a TaN film was formed on the surface of an $SiO_2$/Si substrate by the sputtering technique and then a copper-containing film was deposited on the TaN film by the CVD technique, it was also found that the copper-containing films having a thickness of not more than 100 nm were completely or partially peeled off from the surface of the substrate.

Example 2

A vanadium-containing film was formed on the surface of a substrate S using the CVD apparatus as shown in FIG. 1. In this respect, the substrate S used herein was a wafer ($SiO_2$/Si) having a diameter of 8 inches, on which a silicon oxide film had been formed and then holes and/or grooves having a variety of sizes were formed.

The gate valve 304 of the reaction device 3 was opened and then the substrate S was conveyed into the reaction chamber 301 using a robot positioned in the chamber in the proximity to the reaction chamber. The conveyance of the substrate is desirably carried out in a vacuum for the prevention of any adhesion, onto the surface of the substrate, of gases present in the air such as carbon atom-containing gases (such as CO or $CO_2$), oxygen-containing gases (such as $O_2$), and water ($H_2O$) or for the prevention of any diffusion or penetration of these gases into the interior of the substrate. Accordingly, the substrate was conveyed into the reaction chamber under vacuum conditions, in this Example.

The substrate S conveyed into the reaction chamber 301 was placed on a substrate-placing table 303 positioned within the reaction chamber and provided with a heating means in such a manner that the principal face or the surface of the substrate S faced the shower plate 302, while the back face thereof faced the side of the substrate-placing table. This substrate-placing table was always maintained at a predetermined film-forming temperature.

Then $N_2$ gas discharged from the gas-supply device 1 was introduced into the reaction chamber 301 through the mass flow controller MFC1 while controlling the flow rate thereof to a level of 1500 sccm and the substrate-placing table was heated so that the temperature of the substrate could be controlled to a level of 350° C., while maintaining the reaction chamber at a desired film-forming pressure. After the elapse of a time ranging from 0 to 10 minutes, the film-forming operation was initiated according to the film-forming step 1 specified below. As the raw material, there was used TDEAV (tetrakis-diethylamino vanadium: $V[N(C_2H_5)_2]_4$). In addition, TBH was used as the reducing gas.

Step 1 (Formation of Vanadium-Containing Film):

Using the substrate heated through the foregoing processes, a vanadium-containing film was prepared according to the method carried out under the substrate-producing conditions 1 and 2 specified below:

Substrate-Producing Conditions 1:
  Substrate Used $SiO_2$/Si;
  Amount of Supplied TDEAV: 84 mg/min;
  Flow Rate of Carrier for TDEAV, $N_2$: 400 sccm;
  Flow Rate of TBH: 80 sccm;
  Flow Rate of Carrier, $N_2$: 1500 sccm;
  Film-Forming Pressure: 340 Pa;
  Film-Forming Time: 10 to 20 minutes;
  Film-Forming Temperature: 350° C.
  Film Thickness: 50 to 100 nm There was thus prepared a substrate provided thereon with a vanadium-containing film formed according to the foregoing substrate-producing conditions 1 and also having holes and grooves whose minimum hole-diameter: φ was 0.05 μm and whose aspect ratio (AR) was not less than 4.

The process which makes use of TBH as the reducing gas has been described above, but $NH_3$ may likewise be used in place of TBH to thus form a substrate provided thereon with a vanadium-containing film and also having holes and grooves whose minimum hole-diameter: φ is 0.05 μm and whose aspect ratio is not less than 4.

Moreover, when using TDMAV (tetrakis-dimethylamino vanadium: $V[N(CH_3)_2]_4$) as the raw material instead of TDEAV and carrying out the film-forming process at a temperature of 300° C., a substrate could be prepared, which was provided thereon with holes and grooves whose minimum hole-diameter: φ was 0.05 μm and whose aspect ratio was not less than 4.

Step 2 (Formation of Quality-Modifying Film):

After the completion of the foregoing step 1, the supply of the TDEAV raw material, the carrier for the TDEAV raw material and the reducing gas: TBH was discontinued, while only the carrier gas ($N_2$ gas) was flowing through the reaction chamber at a flow rate of 1500 sccm to thus purge the reaction chamber for one minute and then the surface of the substrate was modified, in succession, while using the following substrate-producing conditions 2 to thus prepare a surface-modified substrate.

Substrate-Producing Conditions 2:
  Substrate: Vanadium-Containing Film/$SiO_2$/Si (Substrate prepared using the substrate-producing conditions 1);
  Amount of Supplied TDEAV: 84 mg/min;
  Flow Rate of Carrier for TDEAV, $N_2$: 400 sccm;
  Flow Rate of Carrier, $N_2$: 1580 sccm;
  Film-Forming Pressure: 340 Pa;
  Film-Forming Time: 1 to 5 minutes;
  Film-Forming Temperature: 350° C.
  Film Thickness: 5 to 25 nm Thus, a substrate could be prepared, which was provided thereon with a surface-modified vanadium-containing film and which was likewise provided with holes and grooves having a minimum hole diameter: φ of 0.05 μm and an aspect ratio of not less than 4.

Similarly, a substrate can be prepared, which is provided with holes and grooves having a minimum hole diameter: φ of 0.05 μm and an aspect ratio of not less than 4, even when $H_2$ gas was substituted for $N_2$ gas as the carrier gas.

When a vanadium-containing film was directly formed on an $SiO_2$/Si, on which holes and grooves had been formed in advance, according to the method carried out under the foregoing substrate-producing conditions 1 and 2, a substrate could be produced, which was provided with a vanadium-containing film having a thickness of 10 nm and likewise provided with holes and grooves whose bottom coverage was not less than 80%.

Example 3

The process for filling holes and/or grooves with a copper-containing film will be described in this Example, while using the substrate provided thereon with a barrier layer and prepared in Example 2.

The following film-forming processes were carried out using the CVD apparatus as shown in FIG. 1. The substrate provided thereon with the vanadium-containing film prepared in Example 2 was conveyed to a copper-containing film-forming reaction chamber through a transportation chamber (maintained at a vacuum) arranged in the proximity of the reaction chamber 301, while paying much attention not to expose the substrate to the air for the prevention of any oxidation of the surface thereof, followed by placing the substrate on the substrate-placing table 303 maintained at a predetermined temperature. Separately, an $SiO_2/Si$ substrate free of any vanadium-containing film was likewise placed on the substrate-placing table 303 of the copper-containing film-forming reaction chamber 301. To these substrates, there was supplied $H_2$ gas while controlling the flow rate thereof and then the substrates were heated up to a set temperature over a predetermined time while maintaining the reaction chamber 301 at a constant pressure. In this case, the pressure of the reaction chamber and the temperature of the substrates were set at the same levels used in the subsequent step for forming a copper-containing film. This $H_2$ gas also serves to remove the oxide film possibly formed on the substrate surface. In this case, $H_2$ gas was used. However, it is also possible to use other gases which have a variety of characteristic properties such that they have a small molecular size, they are quite susceptible to diffusion and they have a high thermal conductivity, and which can release $H^*$ radicals or $H^+$ ions through decomposition or dissociation and specific examples of such gases usable herein include TBH, $NH_3$, $SiH_4$ and hydrazine derivatives.

Then a raw material for forming copper-containing films was supplied onto the surface of the substrates arranged within the reaction chamber 301 in a hydrogen gas atmosphere to thus form a copper-containing film on the substrate surface according to the film-forming method carried out under the film-forming conditions 1 to 3 specified below and to simultaneously fill the holes and grooves present on the substrates with the resulting copper-containing film. In this connection, the raw material was a solution obtained by dissolving 0.5 mole of a complex: $Cu(SOPD)_2$ in octane as a solvent to thus give one liter of an octane solution, which was sealed in a raw material container prior to the practical use thereof. This liquid raw material was discharged from the raw material container 201 and transported to the vaporizer 203 through the piping work, the liquid raw material was then converted into a gas in the vaporizer and supplied onto the surface of the substrates arranged within the reaction chamber 301 to thus form a film.

Film-Forming Conditions 1:
  Substrate Used: Respective substrates prepared in Steps 1 and 2 in Example 2 (under the substrate-producing conditions 1 and 2);
  Amount of Supplied SOPD: 78 mg/min (3.15 cc/min);
  Amount of Supplied SOPD Divided by Surface Area of Substrate: 0.24 mg/min·cm$^2$ (1.0×10$^{-2}$ cc/min·cm$^2$);
  Flow Rate of Carrier for SOPD, $N_2$: 400 sccm;
  Flow Rate of $H_2$: 2500 sccm;
  Partial Pressure of $H_2$: 1497 Pa;
  Ratio: $H_2$/SOPD: 793;
  (Partial Pressure of $H_2$)×($H_2$/SOPD Ratio): 1,187,000
  Film-Forming Pressure: 1780 Pa;
  Film-Forming Time: 15 to 45 minutes;
  Film-Forming Temperature: 150 to 350° C.
Film-Forming Conditions 2:
  Substrate Used Respective substrates prepared in Steps 1 and 2 in Example 2;
  Amount of Supplied SOPD: 57 mg/min (2.3 cc/min);
  Amount of Supplied SOPD Divided by Surface Area of Substrate: 0.17 mg/min·cm$^2$ (7.3×10$^{-3}$ cc/min·cm$^2$);
  Flow Rate of Carrier for SOPD, $N_2$: 200 sccm;
  Flow Rate of $H_2$: 1800 sccm;
  Partial Pressure of $H_2$: 1563 Pa;
  Ratio: $H_2$/SOPD: 785;
  (Partial Pressure of $H_2$)×($H_2$/SOPD Ratio): 1,220,000
  Film-Forming Pressure: 1780 Pa;
  Film-Forming Time: 15 to 60 minutes;
  Film-Forming Temperature: 150 to 350° C.
Film-Forming Conditions 3:
  Substrate Used Respective substrates prepared in Steps 1 and 2 in Example 2;
  Amount of Supplied SOPD: 28 mg/min (1.15 cc/min);
  Amount of Supplied SOPD Divided by Surface Area of Substrate: 0.089 mg/min·cm$^2$ (3.6×10$^{-3}$ cc/min·cm$^2$);
  Flow Rate of Carrier for SOPD, $N_2$: 200 sccm;
  Flow Rate of $H_2$: 1800 sccm;
  Partial Pressure of $H_2$: 1570 Pa;
  Ratio: $H_2$/SOPD: 1570;
  (Partial Pressure of $H_2$)×($H_2$/SOPD Ratio): 2,460,000
  Film-Forming Temperature: 150 to 350° C.
  Film-Forming Pressure: 1780 Pa;
  Film-Forming Time: 15 to 90 minutes;

The holes and grooves formed on or through the substrate were filled with the copper-containing film by the foregoing procedures. The results of the foregoing hole- and/or groove-filling treatments are summarized in the following Tables 4 and 5. Table 4 shows the results obtained when using the substrates produced in the step 1 in Example 2, while Table 5 shows the results obtained when using the substrates produced in the step 2 in Example 2.

In addition, FIG. 5 schematically shows the conditions of holes and/or grooves filled with a copper-containing film. As will be clear from FIG. 5, a copper-containing film is uniformly formed on a barrier layer uniformly deposited on the surface of the substrate including the interior of the holes and grooves formed on or through the substrate so that these holes and/or grooves are filled with the copper-containing film without leaving any space in the holes and/or grooves.

TABLE 4

| Hole Diameter (μm) | Film-Forming Conditions 1 (AR) | Film-Forming Conditions 2 (AR) | Film-Forming Conditions 3 (AR) |
|---|---|---|---|
| ϕ0.05 | ⊚ (18) | ⊚ (14) | X (2) |
| ϕ0.1 | ⊚ (10) | ⊚ (8) | X (2) |
| ϕ0.15 | ⊚ (7) | ⊚ (5) | X (3) |

TABLE 5

| Groove Diameter (μm) | Film-Forming Conditions 1 (AR) | Film-Forming Conditions 2 (AR) | Film-Forming Conditions 3 (AR) |
|---|---|---|---|
| ϕ0.05 | ⊚ (20) | ⊚ (20) | X (5) |
| ϕ0.1 | ⊚ (10) | ⊚ (10) | X (5) |
| ϕ0.15 | ⊚ (7) | ⊚ (7) | X (4) |

In Tables 4 and 5, the conditions of holes or grooves filled with the copper-containing film were evaluated on the basis of the following criteria:
  ⊚: Holes were completely filled with the copper-containing film; and
  X: Holes could not be filled with the film.

In addition, each numerical value given in parentheses means the aspect ratio (AR) at which the holes could completely be filled with the film.

Regarding the data listed in Tables 4 and 5, whether holes and/or grooves were filled with the copper-containing film or not was confirmed by the SEM and TEM techniques. In this respect, there was not observed any void within the copper-containing film charged in the holes and/or grooves.

The film-forming temperature of the copper-containing films, listed in Table 4 and 5 and for which the complete filling of the holes and/or grooves could be confirmed, was found to be 150 to 350° C. After the step for filling the holes and/or grooves with the copper-containing film, any void was not detected at all, even when the resulting film was annealed by heating the same at 500° C. for 3 hours within a hydrogen or nitrogen gas atmosphere having a pressure of 360 Pa.

The films each prepared using the film-forming conditions 1 and 2, for which the complete filling of the holes and/or grooves could be confirmed, and for which the complete filling of these holes and/or grooves could be confirmed even when the aspect ratios thereof were high, were subjected to the determination of sheet resistance values and as a results, they were found to be in the range of from 2 to $7 \mu\Omega \cdot cm$. The distribution of the sheet resistance values was found to be 2 to 10% for the copper-containing film formed, on a substrate having a diameter of 8 inches, under the film-forming conditions for which the complete filling of these holes and/or grooves was confirmed and at a film-forming temperature ranging from 200 to 300° C.

Accordingly, the foregoing results clearly indicate that fine or narrow holes (at the opening, the diameter $\phi=0.05 \mu m$) each having a high aspect ratio on the order of 18, 20 can completely be filled with the copper-containing film if the supplied amount of a complex, such as $Cu(SOPD)_2$ per unit area is set at a level of not less than $9.0 \times 10^{-2}$ mg/min·cm² ($3.6 \times 10^{-3}$ cc/min·cm²; $1.6 \times 10^{-7}$ mole/min·cm²) as expressed in terms of the supplied amount of the complex divided by the film-forming area on the substrate, among other copper-containing film-forming conditions. In addition, the upper limit of the supplied amount of a complex per unit area was found to be $2.0 \times 10^1$ mg/min·cm² ($8.0 \times 10^{-1}$ cc/min·cm²; $3.6 \times 10^{-5}$ mole/min·cm²) because of the deterioration of the film-forming morphology.

Incidentally, if a vanadium-containing film as a barrier layer is formed in the foregoing film-forming process, prior to the formation of a copper-containing film, it has been confirmed that the formation of initial nuclei in the copper-containing film-forming step can considerably be accelerated and the density of the nuclei formed during the initial nucleation stage can significantly be increased within a very short period of time, and there was not observed any peeling off of the copper-containing film from the vanadium-containing film surface on the resulting substrate.

Separately, a copper-containing film was prepared according to the foregoing process used in Example 3 for filling holes and/or grooves with such a copper-containing film, while using a substrate provided thereon with a barrier layer formed using TDMAV (tetrakis-dimethylamino vanadium: $V[N(CH_3)_2]_4$) instead of TDEAV used in Example 2 as the raw material. As a result, it was found that there were obtained the same results described above in connection with the substrate provided thereon with a barrier layer prepared using TDEAV.

Comparative Example 1

A copper-containing film was directly formed on the surface of an $SiO_2$ substrate provided with holes and/or grooves (minimum hole diameter ($\phi$): 0.16 μm; AR: 6) according to the film-forming conditions 1 and 2 which were confirmed to be effective for filling the holes and/or grooves according to the method for filling them with such a copper-containing film described in Example 2, without forming any barrier layer prior to the formation of the copper-containing film. As a result, it was confirmed that the holes and/or grooves could be filled with the same, but it was also found that the copper-containing film was quite easily peeled off from the surface of the substrate.

Alternatively, a copper-containing film was likewise directly formed on the surface of a substrate while using the film-forming conditions 3. In this case, spaces were detected at the bottom portions of holes and/or grooves and therefore, any complete filling thereof was not confirmed at all, in this case.

Example 4

The same procedures used in the steps 1 and 2 described in Example 2 were repeated except for using TDEAT (tetrakis-diethylamino titanium: $Ti[N(C_2H_5)_2]$) in place of the TDEAV used in Example 2 as the raw material to thus form a substrate provided thereon with a barrier layer consisting of a titanium-containing film. In this respect, however, the film-forming temperature was set at 250° C. in the substrate-producing conditions 1 used in Example 2 and the substrate used in the substrate-producing conditions 2 was titanium-containing film/$SiO_2$/Si substrate and the film-forming temperature was set at 250° C. in the substrate-producing conditions 2, while the remaining conditions were all identical to one another.

Thus, substrates were prepared under the substrate-producing conditions 1 and 2 in Example 2, respectively and each of these substrates was provided thereon with holes and grooves having a minimum hole diameter $\phi$ of 0.05 μm and an aspect ratio (AR) of not less than 4.

In this Example, a substrate provided thereon with holes and grooves having a minimum hole diameter $\phi$ of 0.05 μm and an aspect ratio of not less than 4 can likewise be produced using TBH or $NH_3$ as the reducing gas by the same procedures used in Example 2.

Moreover, the same procedures used in Example 2 were repeated except that TDMAT (tetrakis-dimethylamino titanium: $Ti[N(CH_3)_2]_4$) was used in place of the TDEAT used in Example 2 as the raw material and that the film-forming temperature was changed to 300° C. As a result, a substrate similar to that produced in Example 2 could be produced or a substrate provided thereon with holes and grooves having a minimum hole diameter $\phi$ of 0.05 μm and an aspect ratio of not less than 4 could be obtained.

Example 5

The process for filling holes and/or grooves with a copper-containing film will be described in this Example, while using the substrate provided thereon with a titanium-containing film (using TDEAT as the raw material) and prepared in Example 4.

The same process used in Example 3 were repeated under the conditions completely identical to the film-forming conditions 1 to 3 used in Example 3 except for using a substrate provided thereon with a titanium-containing film instead of the substrate used in Example 3, to thus form a copper-containing film on the surface of the substrate.

The holes and grooves formed on or through the substrate were filled with the copper-containing film by the foregoing procedures. The results of the foregoing hole- and/or groove-filling treatments are summarized in the following Tables 6 and 7. Table 6 shows the results obtained when using the substrates used in Example 4 or produced in the step 1 described in Example 2, while Table 7 shows the results obtained when using the substrates used in Example 4 or produced in the step 2 described in Example 2.

In addition, the conditions of holes and/or grooves filled with a copper-containing film are the same as those schematically shown in FIG. 5. As will be clear from the same, a copper-containing film is uniformly formed on a barrier layer uniformly deposited on the surface of the substrate including the interior of the holes and grooves formed on or through the substrate so that these holes and/or grooves are filled with the copper-containing film without leaving any space in the holes and/or grooves.

TABLE 6

| Hole Diameter ($\mu$m) | Film-Forming Conditions 1 (AR) | Film-Forming Conditions 2 (AR) | Film-Forming Conditions 3 (AR) |
| --- | --- | --- | --- |
| $\phi$0.05 | ◎ (18) | ◎ (14) | X (3) |
| $\phi$0.1 | ◎ (10) | ◎ (8) | X (4) |
| $\phi$0.15 | ◎ (7) | ◎ (5) | X (5) |

TABLE 7

| Groove Diameter ($\mu$m) | Film-Forming Conditions 1 (AR) | Film-Forming Conditions 2 (AR) | Film-Forming Conditions 3 (AR) |
| --- | --- | --- | --- |
| $\phi$0.05 | ◎ (20) | ◎ (20) | X (5) |
| $\phi$0.1 | ◎ (10) | ◎ (10) | X (5) |
| $\phi$0.15 | ◎ (7) | ◎ (7) | X (3) |

In Tables 6 and 7, the conditions of holes or grooves filled with the copper-containing film were evaluated on the basis of the following criteria:

◎: Holes were completely filled with the copper-containing film; and

X: Holes could not be filled with the film.

In addition, each numerical value given in parentheses means the aspect ratio (AR) at which the holes could completely be filled with the film.

Regarding the data listed in Tables 6 and 7, whether holes and/or grooves were filled with the copper-containing film or not was confirmed by the SEM and TEM techniques. In this respect, there was not observed any void within the copper-containing film charged in the holes and/or grooves.

The film-forming temperature of the copper-containing films, listed in Table 6 and 7 and for which the complete filling of the holes and/or grooves could be confirmed, was found to be 150 to 350° C. After the step for filling the holes and/or grooves with the copper-containing film, any void was not detected at all, even when the resulting film was annealed by heating the same at 500° C. for 3 hours within a hydrogen or nitrogen gas atmosphere having a pressure of 360 Pa.

The films each prepared using the film-forming conditions 1 and 2, for which the complete filling of the holes and/or grooves could be confirmed, and for which the complete filling of these holes and/or grooves could be confirmed even when the aspect ratios thereof were high, were subjected to the determination of sheet resistance values and as a results, they were found to be in the range of from 2 to 10$\mu\Omega\cdot$cm. The distribution of the sheet resistance values was found to be 2 to 12% for the copper-containing film formed, on a substrate having a diameter of 8 inches, under the film-forming conditions for which the complete filling of these holes and/or grooves was confirmed and at a film-forming temperature ranging from 200 to 300° C.

Accordingly, the foregoing results clearly indicate that fine or narrow holes (at the opening, the diameter $\phi$=0.05 $\mu$m) each having a high aspect ratio on the order of 18, 20 can completely be filled with the copper-containing film if the supplied amount of a complex, such as Cu(SOPD)$_2$ per unit area is set at a level of not less than $9.0 \times 10^{-2}$ mg/min·cm$^2$ ($3.6 \times 10^{-3}$ cc/min·cm$^2$; $1.6 \times 10^{-7}$ mole/min·cm$^2$) as expressed in terms of the supplied amount of the complex divided by the film-forming area on the substrate, among other copper-containing film-forming conditions. In addition, the upper limit of the supplied amount of a complex per unit area was found to be $2.0 \times 10^1$ mg/min·cm$^2$ ($8.0 \times 10^{-1}$ cc/min·cm$^2$; $3.6 \times 10^{-5}$ mole/min·cm$^2$) because of the deterioration of the film-forming morphology.

Incidentally, if a titanium-containing film as a barrier layer is formed in the foregoing film-forming process, prior to the formation of a copper-containing film, it has been confirmed that the formation of initial nuclei in the copper-containing film-forming step can considerably be accelerated and the density of the nuclei formed during the initial nucleation stage can significantly be increased within a very short period of time, and there was not observed any peeling off of the copper-containing film from the titanium-containing film surface on the resulting substrate.

Separately, a copper-containing film was formed, according to the process used in Example 5 for filling holes with the copper-containing film, while using a substrate provided thereon with a barrier layer formed using TDMAT (tetrakis-dimethylamino titanium: Ti[N(CH$_3$)$_2$]$_4$) in place of the TDEAT as the raw material used in process described in Example 4. As a result, there were obtained the same results described above.

INDUSTRIAL APPLICABILITY

The present invention permits the formation of copper-containing distributing wires possessing desired characteristic properties including excellent filling properties and excellent adhesion between the barrier layer (adherent layer) as a primary coat and the distributing wires and therefore, the method according to the present invention can be applied to the field of metal distributing wires and, in particular, to the field of copper-distributing wires typical of those used in the semiconductor industries such as semiconductor elements (for instance, LSI, IC or the like).

EXPLANATION OF SYMBOLS

Figure 1:
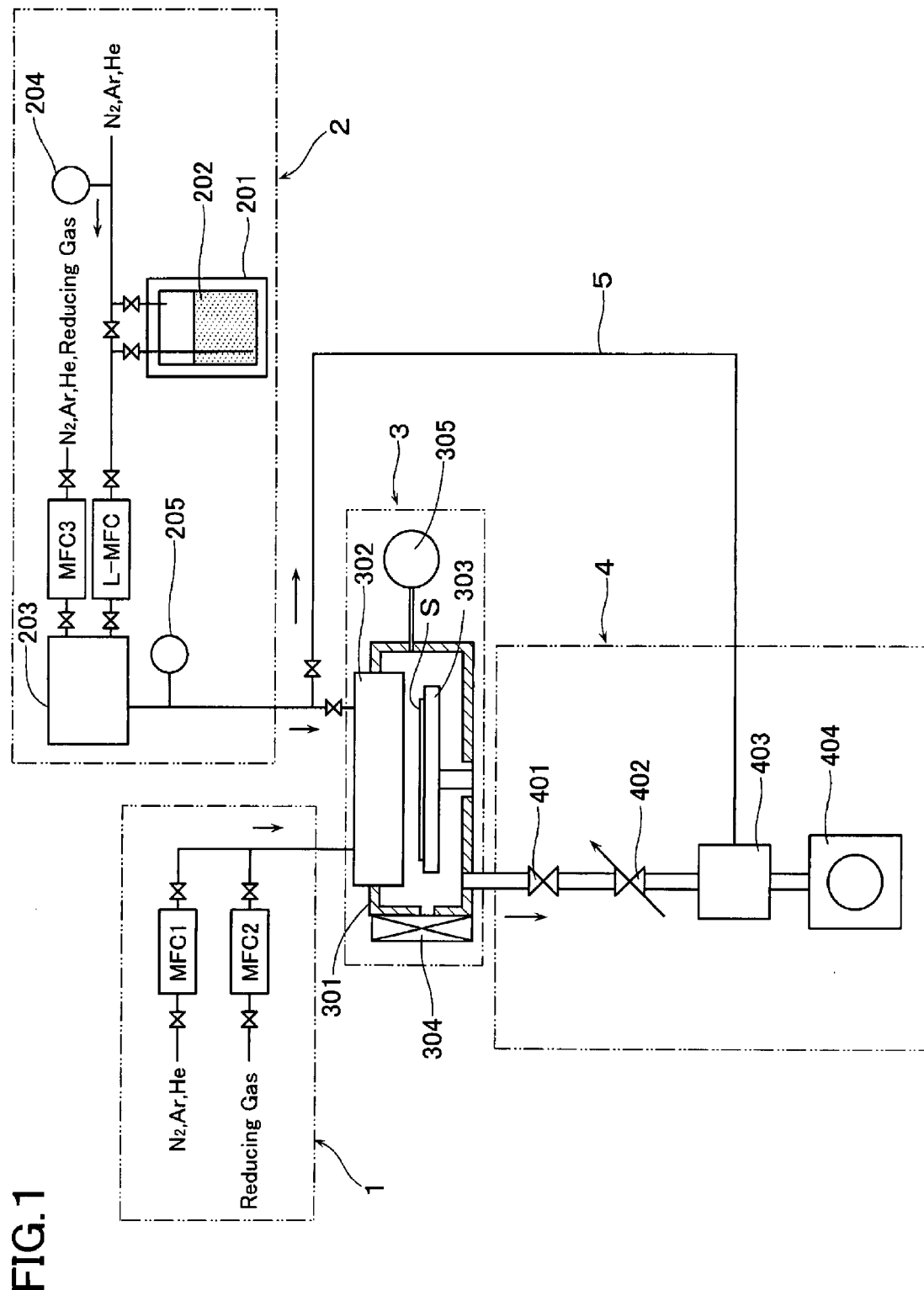
FIG. 1 is an arrangement plan schematically showing the structure of an embodiment of a CVD apparatus used for forming a copper-containing film and/or a barrier layer according to the present invention.
Figure 2:
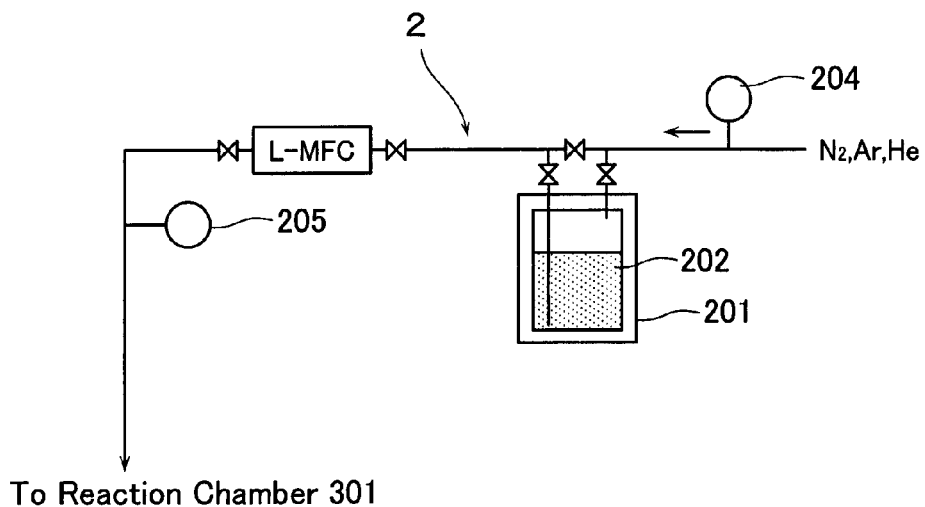
FIG. 2 is an arrangement plan schematically showing another embodiment of the raw material-supplying device fitted to the CVD apparatus as shown in FIG. 1.
Figure 3:
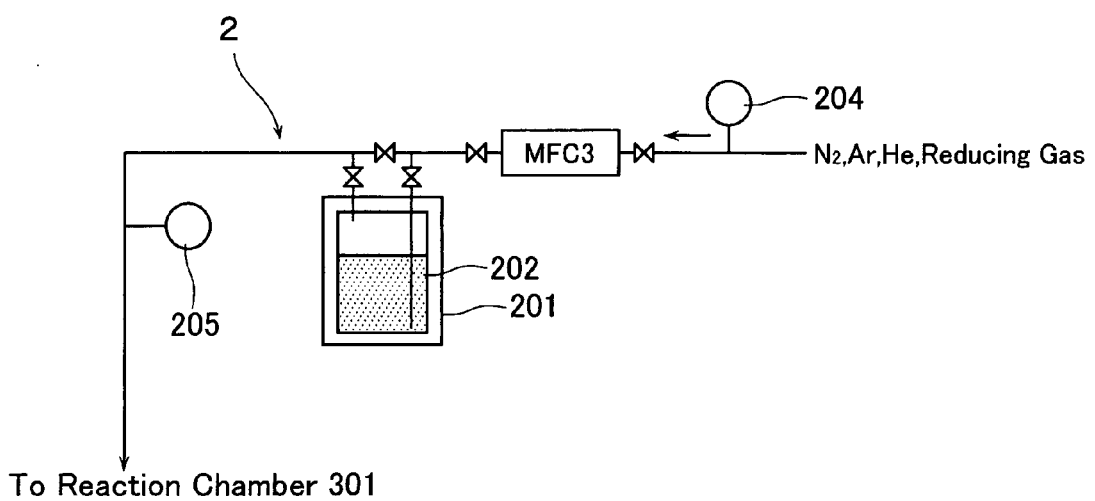
FIG. 3 is an arrangement plan schematically showing still another embodiment of the raw material-supplying device fitted to the CVD apparatus as shown in FIG. 1.
Figure 4:
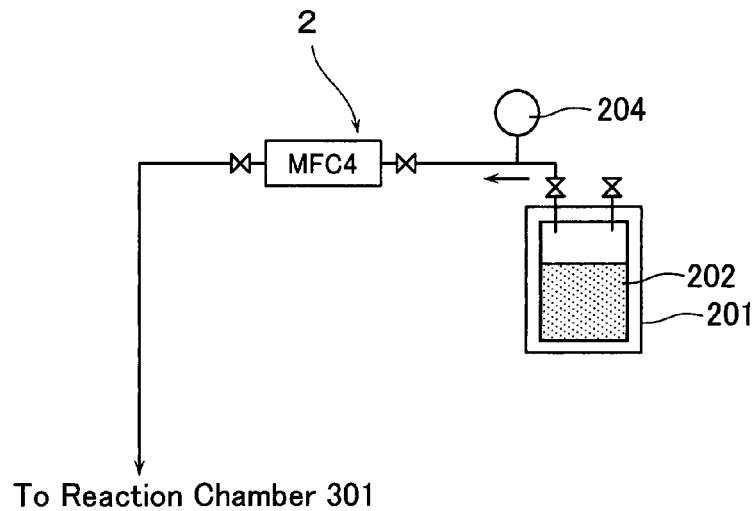
FIG. 4 is an arrangement plan schematically showing a still further embodiment of the raw material-supplying device fitted to the CVD apparatus as shown in FIG. 1.
Figure 5:
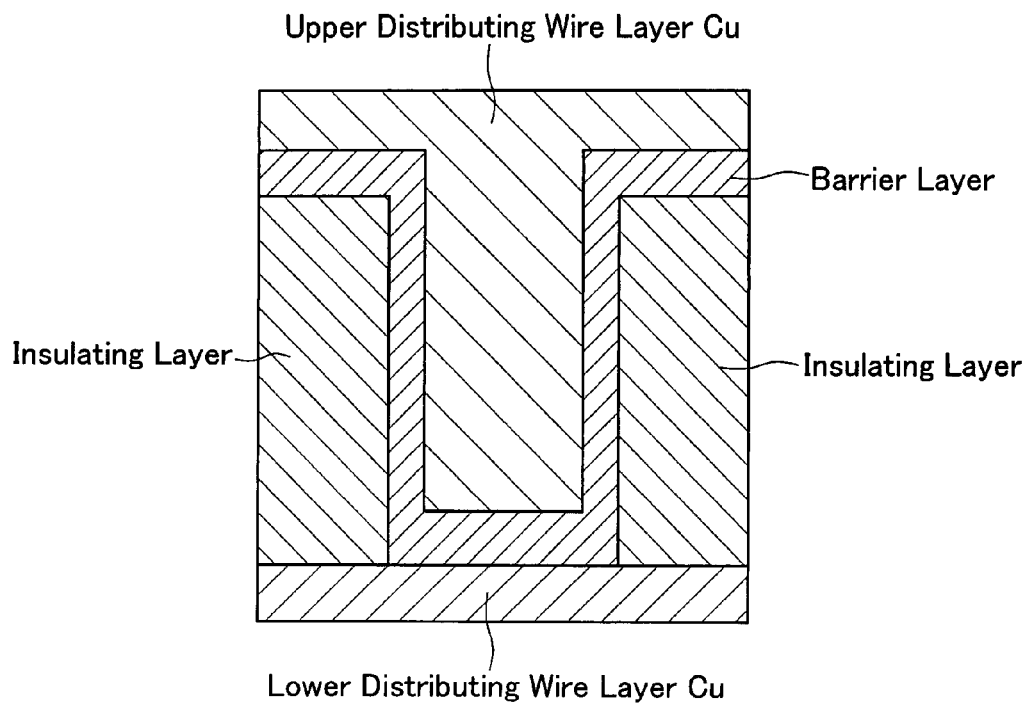
FIG. 5 is a cross sectional view schematically showing a hole or a groove filled with a copper-containing film according to the present invention.
Figure 6:
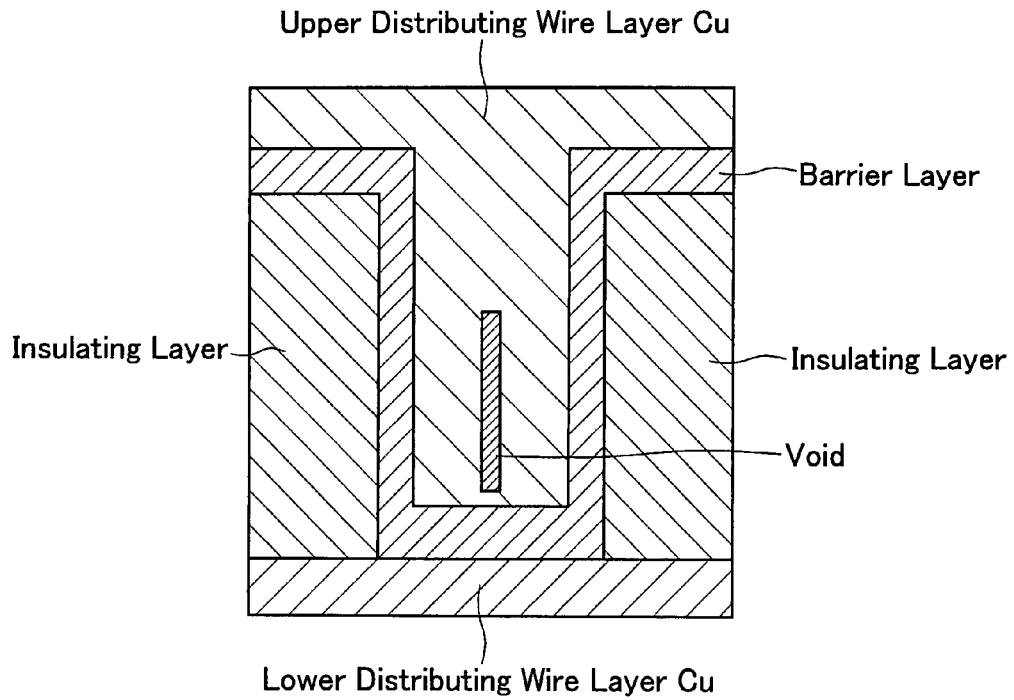
FIG. 6 is a cross sectional view schematically showing a void formed when a hole present on a conventional barrier layer is filled with a conventional copper-containing film, which is used for forming copper distributing wires.
Figure 7:
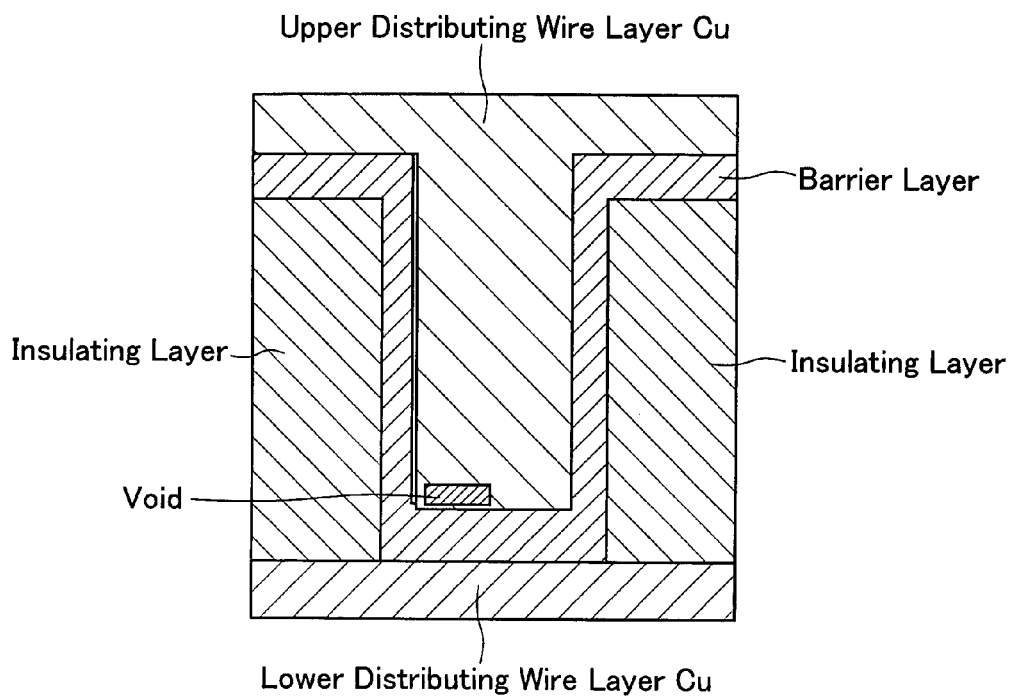
FIG. 7 is a cross sectional view schematically showing a void formed when forming conventional copper distributing wires and then subjecting the same to an annealing treatment.

1 . . . Gas-supply Device; 2 . . . Raw Material-Supply Device; 201 . . . Raw Material Container; 202 . . . Raw Material; 203 . . . Vaporizer; 3 . . . . Reaction device; 301 . . . Reaction Chamber; 302 . . . Shower Plate; 303 . . . Substrate-Placing Table; 304 . . . Gate Valve; 4 . . . Exhaust Device; 401 . . . Discharge Valve; 402 . . . Pressure-Control Valve; 403 . . . Raw Material Trap; 404 . . . Vacuum Pump

What is claimed is:

1. A copper distributing wire-forming method comprising the steps of forming a primary coat which consists of a vanadium- or titanium-containing film on a subject on which a film is to be formed, the film carrying holes and/or grooves formed thereon in advance, according to a CVD technique while using a raw gas consisting of a tetravalent amide vanadium-containing organometal compound or a tetravalent amide titanium-containing organometal compound as well as a reducing gas; and then forming a copper-containing film thereon by a CVD technique to thus fill the holes and/or grooves with the copper-containing film, wherein the copper-containing film is formed, on the subject on which a film is to be formed, according to the CVD technique while using a gas consisting of a copper complex represented by a following general formula (I-a), wherein in the general formula (I-a), X, Y and Z are the same as those defined below in connection with a following general formula (I-a)', wherein formula (I-a) possesses, as a ligand, β-diketonate group represented by the general formula (I-a)' in which Z represents a hydrogen atom or an alkyl group having 1 to 4 carbon atoms; and X and Y, which may be the same or different from one another, each represent a linear or branched alkyl group having 1 to 8 carbon atoms or a $C_{1-8}$ alkyl group in which at most 9 hydrogen atoms thereof may be substituted with fluorine atoms:

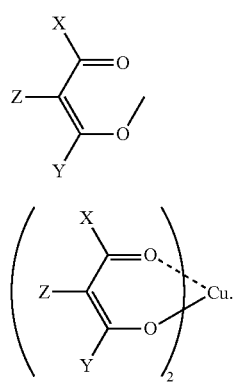

2. The copper distributing wire-forming method as set forth in claim 1, wherein the tetravalent amide vanadium-containing organometal compound as a raw material is tetrakis-diethyl-amino vanadium, tetrakis-dimethyl-amino vanadium or tetrakis-ethylmethyl-amino vanadium; and the tetravalent amide titanium-containing organometal compound is tetrakis-diethyl-amino titanium, tetrakis-dimethyl-amino titanium or tetrakis-ethylmethyl-amino titanium.

3. The copper distributing wire-forming method as set forth in claim 1, wherein the reducing gas is one capable of generating H* radicals or H⁺ ions through decomposition or dissociation.

4. The copper distributing wire-forming method as set forth in claim 3, wherein the reducing gas is a gas selected from the group consisting of hydrazine derivatives, $NH_3$, $H_2$, $SiH_4$ and $Si_2H_6$.

5. The copper distributing wire-forming method as set forth in claim 4, wherein the hydrazine derivative is hydrazine, one or two hydrogen atoms of which are substituted with a substituent selected from the group consisting of methyl group, ethyl group and linear or branched butyl group.

6. The copper distributing wire-forming method as set forth in claim 4, wherein the hydrazine derivative is tertiary butyl hydrazine.

7. The copper distributing wire-forming method as set forth in claim 1, wherein the tetravalent amide vanadium- or titanium-containing organometal compound is reacted with the reducing gas at a temperature falling within a range in which a film-forming rate varies depending on a temperature of the subject on which a desired film is to be formed, to thus form the vanadium- or titanium-containing film.

8. A copper distributing wire-forming method comprising the steps of forming a primary coat which consists of a vanadium- or titanium-containing film on a subject on which a film is to be formed, the film carrying holes and/or grooves formed thereon in advance, according to a CVD technique while using a raw gas consisting of a tetravalent amide vanadium-containing organometal compound or a tetravalent amide titanium-containing organometal compound as well as a reducing gas; and then forming a copper-containing film thereon by a CVD technique to thus fill the holes and/or grooves with the copper-containing film, wherein the copper-containing film is formed, on the subject on which a film is to be formed, according to the CVD technique while using a gas consisting of a copper complex represented by a following general formula (I-b), wherein in the general formula (I-b), X, Y and Z are the same as those defined below in connection with a following general formula (I-b)', wherein formula (I-b) possesses, as a ligand, β-diketonate group represented by the general formula (I-b)' in which Z represents a hydrogen atom or an alkyl group having 1 to 4 carbon atoms; and X and Y, which may be the same or different from one another, each represent a group denoted by a formula: $C_nH_{2n}$—O—$C_mH_{2m+1}$, wherein in the formula, n ranges from 1 to 8; m ranges from 0 to 7, provided that n+m is equal to or smaller than 8 or wherein at most 9 hydrogen atoms thereof may be substituted with fluorine atoms:

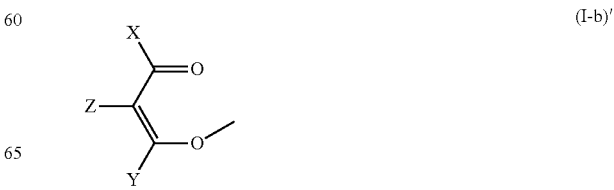

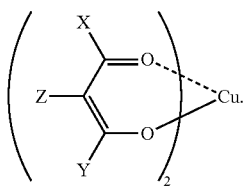

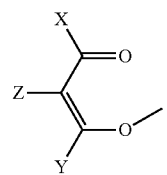

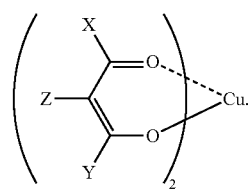

9. The copper distributing wire-forming method as set forth in claim 8, wherein the reducing gas is one capable of generating H* radicals or H⁺ ions through decomposition or dissociation.

10. The copper distributing wire-forming method as set forth in claim 9, wherein the reducing gas is a gas selected from the group consisting of hydrazine derivatives, $NH_3$, $H_2$, $SiH_4$ and $Si_2H_6$.

11. The copper distributing wire-forming method as set forth in claim 10, wherein the hydrazine derivative is hydrazine, one or two hydrogen atoms of which are substituted with a substituent selected from the group consisting of methyl group, ethyl group and linear or branched butyl group.

12. The copper distributing wire-forming method as set forth in claim 10, wherein the hydrazine derivative is tertiary butyl hydrazine.

13. The copper distributing wire-forming method as set forth in claim 8, wherein the hydrazine derivative is tertiary butyl hydrazine.

14. The copper distributing wire-forming method as set forth in claim 8, wherein the tetravalent amide vanadium- or titanium-containing organometal compound is reacted with the reducing gas at a temperature falling within a range in which a film-forming rate varies depending on a temperature of the subject on which a desired film is to be formed, to thus form the vanadium- or titanium-containing film.

15. A copper distributing wire-forming method comprising the steps of forming a primary coat which consists of a vanadium- or titanium-containing film on a subject on which a film is to be formed, the film carrying holes and/or grooves formed thereon in advance, according to a CVD technique while using a raw gas consisting of a tetravalent amide vanadium-containing organometal compound or a tetravalent amide titanium-containing organometal compound as well as a reducing gas; and then forming a copper-containing film thereon by a CVD technique to thus fill the holes and/or grooves with the copper-containing film, wherein the copper-containing film is formed, on the subject on which a film is to be formed, according to the CVD technique while using a gas consisting of a copper complex represented by a following general formula (I-c) (in Formula (I-c), the substituents X, Y and Z are the same as those defined below in connection with a following general formula (I-c)'), which possesses, as a ligand, β-diketonate group represented by the general formula (I-c)' in which Z represents a hydrogen atom or an alkyl group having 1 to 4 carbon atoms; and X and Y, which may be the same or different from one another, each represent a group denoted by a formula: $C_nH_{2n}$—CH=CH—$C_mH_{2m+1}$ (in the formula, n ranges from 0 to 6; m ranges from 0 to 6, provided that n+m is equal to or smaller than 6) or the foregoing group denoted by the formula: $C_nH_{2n}$—CH=CH—$C_mH_{2m+1}$ in which at most 9 hydrogen atoms thereof may be substituted with fluorine atoms:

16. The copper distributing wire-forming method as set forth in claim 15, wherein the tetravalent amide vanadium-containing organometal compound as a raw material is tetrakis-diethyl-amino vanadium, tetrakis-dimethyl-amino vanadium or tetrakis-ethylmethyl-amino vanadium; and the tetravalent amide titanium-containing organometal compound is tetrakis-diethyl-amino titanium, tetrakis-dimethyl-amino titanium or tetrakis-ethylmethyl-amino titanium.

17. The copper distributing wire-forming method as set forth in claim 15, wherein the reducing gas is one capable of generating H* radicals or H⁺ ions through decomposition or dissociation.

18. The copper distributing wire-forming method as set forth in claim 15, wherein the reducing gas is a gas selected from the group consisting of hydrazine derivatives, $NH_3$, $H_2$, $SiH_4$ and $Si_2H_6$.

19. The copper distributing wire-forming method as set forth in claim 15, wherein the hydrazine derivative is hydrazine, one or two hydrogen atoms of which are substituted with a substituent selected from the group consisting of methyl group, ethyl group and linear or branched butyl group.

20. The copper distributing wire-forming method as set forth in claim 15, wherein the hydrazine derivative is tertiary butyl hydrazine.

21. The copper distributing wire-forming method as set forth in claim 15, wherein the tetravalent amide vanadium- or titanium-containing organometal compound is reacted with the reducing gas at a temperature falling within a range in which a film-forming rate varies depending on a temperature of the subject on which a desired film is to be formed, to thus form the vanadium- or titanium-containing film.

22. The copper distributing wire-forming method as set forth in any one of claims 1, 8, and 15, wherein a supplied amount of the raw material for forming the copper-containing film as set forth in claim 1 and those of the copper complexes represented by the general formulas (I), (I-a), (I-b) and (I-c) as set forth in any one of claims 8 to 11 are ones which can satisfy a following relation as expressed in terms of the amount thereof per unit area of the film-forming surface on the subject on which the copper-containing film is to be formed:

$$8.0 \times 10^{-1} cc/min \times cm^2 (3.6 \times 10^{-5} mol/min \times cm^2) \geq \text{(Amount to be Supplied)} \geq 3.6 \times 10^{-3} cc/min \times cm^2 (1.6 \times 10^{-7} mol/min \times cm^2).$$

23. The copper distributing wire-forming method as set forth in claim 22, wherein a film-forming temperature ranges from 150 to 350° C. when forming the copper-containing film, according to the CVD technique.

24. The copper distributing wire-forming method as set forth in claim 23, wherein a hydrogen atom-containing gas is used as the reducing gas when forming the copper-containing film.

25. The copper distributing wire-forming method as set forth in claim 24, wherein the hydrogen atom-containing gas is $H_2$ gas.

* * * * *